(12) United States Patent
Wilsey

(10) Patent No.: US 9,416,397 B2
(45) Date of Patent: Aug. 16, 2016

(54) METHODS OF DETERMINING GLUCOSE AND KETONE VALUES IN A SAMPLE

(71) Applicant: Roche Diabetes Care, Inc., Indianapolis, IN (US)

(72) Inventor: Christopher D. Wilsey, Carmel, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/549,724

(22) Filed: Nov. 21, 2014

(65) Prior Publication Data

US 2015/0140584 A1    May 21, 2015

Related U.S. Application Data

(62) Division of application No. 13/667,057, filed on Nov. 2, 2012, now Pat. No. 8,921,061.

(51) Int. Cl.
*C12Q 1/54* (2006.01)
*C12Q 1/00* (2006.01)

(52) U.S. Cl.
CPC . *C12Q 1/54* (2013.01); *C12Q 1/006* (2013.01)

(58) Field of Classification Search
None
See application file for complete search history.

(56) References Cited

U.S. PATENT DOCUMENTS

| | | | |
|---|---|---|---|
| 4,397,956 A | 8/1983 | Maggio | |
| 5,071,769 A | 12/1991 | Kundu et al. | |
| 5,633,143 A | 5/1997 | Ueda et al. | |
| 6,540,891 B1 | 4/2003 | Stewart et al. | |
| 6,541,216 B1 | 4/2003 | Wilsey et al. | |
| 6,736,957 B1 | 5/2004 | Forrow et al. | |
| 6,762,035 B1 | 7/2004 | Gupta | |
| 6,984,307 B2 | 1/2006 | Zweig | |
| 7,504,019 B2 | 3/2009 | Forrow et al. | |
| 7,553,615 B2 | 6/2009 | Heindl et al. | |
| 7,727,467 B2 | 6/2010 | Burke et al. | |
| 8,008,037 B2 | 8/2011 | Wilsey et al. | |
| 8,809,013 B2 | 8/2014 | Heindl et al. | |
| 2003/0068666 A1 | 4/2003 | Zweig | |
| 2004/0118704 A1 | 6/2004 | Wang et al. | |
| 2006/0051738 A1 | 3/2006 | Zweig | |
| 2007/0289881 A1 | 12/2007 | Forrow et al. | |
| 2008/0213809 A1 | 9/2008 | Heindl et al. | |
| 2010/0270175 A1 | 10/2010 | Pei et al. | |
| 2011/0031133 A1 | 2/2011 | Forrow et al. | |
| 2011/0079522 A1 | 4/2011 | Webster et al. | |
| 2011/0094882 A1 | 4/2011 | Macfie et al. | |
| 2011/0094896 A1 | 4/2011 | Macfie et al. | |
| 2011/0143416 A1 | 6/2011 | Horn et al. | |
| 2012/0241335 A1 | 9/2012 | Horn et al. | |
| 2012/0276565 A1 | 11/2012 | Roedel et al. | |

FOREIGN PATENT DOCUMENTS

| | | |
|---|---|---|
| CN | 102741694 A | 10/2012 |
| EP | 279069 | 7/1994 |
| EP | 1023455 | 5/2007 |
| EP | 1801229 | 6/2007 |
| EP | 2308991 | 4/2011 |
| EP | 2317313 | 4/2011 |
| EP | 2317315 A1 | 5/2011 |
| WO | 01/46457 A2 | 6/2001 |
| WO | 01/73114 | 10/2001 |
| WO | 2012/003306 | 1/2012 |

*Primary Examiner* — Nashaat Nashed

(57) ABSTRACT

Reagent materials and associated test elements are provided. In one embodiment, a test element having dual functionality includes a first coenzyme-dependent enzyme or a substrate for the first enzyme, a second coenzyme-dependent enzyme or a substrate for the second enzyme, and a coenzyme selected from the group consisting of thio-NAD, thio-NADP, and a compound according to formula (I). In one aspect, the first analyte is hydroxybutyrate and the first enzyme is a hydroxybutyrate dehydrogenase, and the second analyte is glucose and the second enzyme is a glucose dehydrogenase or a glucose oxidase. Other aspects of the subject application are directed to unique reagent materials. Further embodiments, forms, objects, features, advantages, aspects, and benefits shall become apparent from the description and drawings.

9 Claims, 18 Drawing Sheets

METHODS OF DETERMINING GLUCOSE AND KETONE VALUES IN A SAMPLE

CROSS-REFERENCE TO RELATED APPLICATIONS

This patent application is a divisional of U.S. patent application Ser. No. 13/667,057 (filed 2 Nov. 2012), now U.S. Pat. No. 8,921,061 (issued 30 Dec. 2014), which is incorporated herein by reference as if set forth in its entirety.

BACKGROUND

The use of disposable test elements has become commonplace to measure the presence and/or concentrations of selected analytes in test samples. For example, patients suffering from diabetes and similar medical conditions often engage in self-monitoring of blood glucose where the patient monitors his or her blood glucose levels. The purpose of monitoring blood-glucose levels is to determine the concentration level and if necessary to take corrective action if the level is too high or too low in order to bring the level back within an acceptable range. The failure to take corrective action can have serious medical implications. Glucose monitoring is a fact of everyday life for diabetic individuals, and the accuracy of such monitoring can literally mean the difference between life and death. Failure to maintain blood glucose at acceptable levels on a regular basis can result in serious diabetes-related complications, including cardiovascular disease, kidney disease, nerve damage and blindness.

People with diabetes who intensively manage their blood sugar experience long-lasting benefits. The Diabetes Control and Complications Trial (DCCT) was a clinical study conducted from 1983 to 1993 by the National Institute of Diabetes and Digestive and Kidney Diseases (NIDDK). The DCCT compared intensive to conventional treatments. Patients on intensive treatment kept glucose levels as close to normal as possible with at least three insulin injections a day or an insulin pump, and frequent self-monitoring of blood glucose levels. Intensive treatment aimed to keep hemoglobin A1c (HbA1c), which reflects average blood glucose over a 2- to 3-month period, as close to normal as possible. Conventional treatment consisted of one or two insulin injections a day with once-a-day urine or blood glucose testing. The results of the DCCT study showed that keeping blood glucose levels as close to normal as possible slows the onset and progression of eye, kidney, and nerve diseases caused by diabetes. In fact, it demonstrated that any sustained lowering of blood glucose helps, even if the person has a history of poor control.

A number of analytical instruments or biosensors, such as glucose meters, are currently available that permit an individual to test the glucose level in a small sample of blood. Many of the meter designs currently available make use of a disposable test element which, in combination with the meter, measures the amount of glucose in the blood sample electrochemically or optically. In current glucose meters, the information displayed as a consequence of a successful blood glucose measurement is the respective blood glucose value, typically shown in mg/dL or mmol units, and perhaps the time and date the measurement was performed. This information, in combination with calculation of planned or known intake of carbohydrates or planned or known activities and knowledge of other situational or individual factors, is in most cases sufficient to allow diabetics to adjust or derive their dietary intake and/or an immediate dose of insulin to inject to control blood glucose level on the short-term. Also, in case of low glucose values, diabetics can detect the need for intake of sugar to avoid hypoglycemia.

An absence or insufficient amount of insulin prevents the body from using glucose as a fuel source to produce energy. When this occurs, the body produces energy by breaking down fatty acids, which results in ketone byproducts and increased ketone levels. Increased ketone levels in diabetics may also be caused by a heart attack, stroke, recreational drug usage or an intercurrent illness such as pneumonia, influenza, gastroenteritis, or a urological infection. Excessive ketone levels in diabetics leads to an episode of diabetic ketoacidosis (DKA), a medical emergency that can result in death if not treated. Symptoms of DKA include nausea, vomiting, excessive thirst and urine production, abdominal pain, labored breathing, fatigue, and coma, amongst others. Given the seriousness of DKA, it is desirable to administer treatment to reduce ketone levels before the full onset of a DKA episode. Further, since symptoms related to a DKA episode may not present until the DKA episode has onset or ketone levels are otherwise undesirably high, it is generally preferred for ketone reducing treatment not to begin as a response to these symptoms.

Prevention of DKA episodes can be achieved by measuring ketone levels and seeking medical attention if they rise above a certain concentration. Urine tests can be utilized to determine ketone levels. The ADA website recommends that ketone levels should be checked every 4-6 hours when a diabetic has an illness (such as a cold or the flu), or when his or her blood glucose is more than 240 mg/dl. (available on the World Wide Web at diabetes.org/living-with-diabetes/complications/ketoacidosis-dka.html). However, for diabetics who perform multiple blood glucose tests per day, performing separate urine tests in addition to their blood glucose tests is time consuming and burdensome.

By having a dual test to measure glucose and ketone levels on the same test strip, a diabetic is better enabled to comply with testing recommendations and safer therapy by detecting high ketone levels early. For example, it is recommended to avoid exercise when ketone and blood glucose are high because elevated levels of these analytes may be indicative that diabetes management is unsatisfactory. However, most diabetics do not have ketone tests readily available for testing, and often do not have information readily available for how to handle such situations.

The use of separate urine tests for determining ketone levels also requires additional diagnostic supplies and their attendant costs, and makes it difficult to correlate blood glucose and ketone levels. It is also possible to determine ketone levels from blood samples. When blood samples are used, ketone levels are commonly determined by measuring the concentration of hydroxybutyrate, which is the predominate ketone in blood. Hydroxybutyrate concentrations below 0.6 mM in blood are considered normal, while hydroxybutyrate concentrations that are between 0.6 mM and 1.5 mM indicate that a problem may develop and greater than 1.5 mM indicate a risk for developing DKA. Hydroxybutyrate concentrations above 3 mM in blood are indicative or DKA and require emergency medical treatment.

Current techniques for determining ketone levels from blood involve single function test elements that are suitable for detecting hydroxybutyrate concentrations for example. Much like the urine test described above however, diabetics who perform a relatively high magnitude of blood glucose tests per day may find it time consuming and burdensome to perform separate ketone level blood tests in addition to their blood glucose tests, particularly since current blood ketone tests are slower than state of the art blood glucose tests. Ketone level blood tests that are performed independent of blood glucose tests also require additional diagnostic supplies and additional expenses attendant therewith must be incurred. Moreover, performing separate tests for determining blood glucose and blood ketone levels makes it difficult to correlate the measured blood glucose and blood ketone values.

Other techniques for determining ketone levels from blood involve test elements suitable for detecting blood glucose and blood ketone levels. In these current test elements however, blood glucose levels are measured more quickly than blood ketone levels such that the blood ketone test results are delayed and provided after the blood glucose test results. Alternatively, the results of both the blood glucose and blood ketone tests are not provided until the latter completion of the blood ketone test. In either case, waiting for the results of one or both tests until the blood ketone test is completed can become quite burdensome and time consuming for a diabetic who performs a relatively high magnitude of tests each day, particularly when considering that in some instances the blood ketone test can take almost twice as long to complete as the blood glucose test. Moreover, when the blood glucose test results are provided before and separate from the blood ketone rest results, a possibility arises for a user to discontinue testing before the blood ketone test is completed and/or divert attention elsewhere after the blood glucose test results have been provided but before the results of the blood ketone test have been properly considered.

Given the ramifications of accurate recording, reporting and analyzing of blood ketone measurements in addition to blood glucose measurements, improvements in the techniques, procedures and equipment for testing blood ketone levels and/or blood ketone and blood glucose levels are desired.

SUMMARY

Reagent materials and associated test elements are provided. In one embodiment, a test element having dual functionality includes a first coenzyme-dependent enzyme or a substrate for the first enzyme, a second coenzyme-dependent enzyme or a substrate for the second enzyme, and a coenzyme selected from the group consisting of thio-NAD, thio-NADP, and a compound according to formula (I) (hereinafter defined). In one aspect, the first analyte is hydroxybutyrate and the first enzyme is a hydroxybutyrate dehydrogenase, and the second analyte is glucose and the second enzyme is a glucose dehydrogenase or a glucose oxidase. Other aspects of the subject application are directed to unique reagent materials.

In one embodiment, a test element configured for determining first and second analytes includes a first coenzyme-dependent enzyme or a substrate for the first enzyme and a second coenzyme-dependent enzyme or a substrate for the second enzyme. The test element also includes a coenzyme selected from the group consisting of thio-NAD, thio-NADP, and a compound according to formula (I):

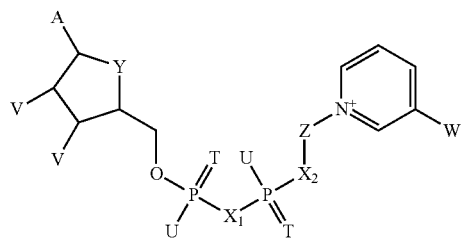

in which
A=adenine or an analog thereof,
T=in each case independently denotes O or S,
U=in each case independently denotes OH, SH, $BH_3^-$, or $BCNH_2^-$,
V=in each case independently denotes OH or a phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
where R4=in each case independently denotes H, F, Cl, or $CH_3$, provided that Z and the pyridine residue are not linked by a glycosidic bond,
or a salt or optionally a reduced form thereof.

In one form of this embodiment, the first analyte is hydroxybutyrate and the first enzyme is a hydroxybutyrate dehydrogenase. In one aspect of this form, the hydroxybutyrate dehydrogenase is 3-hydroxybutyrate dehydrogenase. In another aspect of this form, the second enzyme is a dehydrogenase selected from the group consisting of glucose dehydrogenase, lactate dehydrogenase, malate dehydrogenase, glycerol dehydrogenase, alcohol dehydrogenase, sorbitol dehydrogenase, and an amino acid dehydrogenase comprising L-amino acid dehydrogenase. In still another aspect of this form, the second analyte is glucose and the second enzyme is a glucose dehydrogenase or a glucose oxidase. In a further aspect, the coenzyme is a compound according to formula (I)

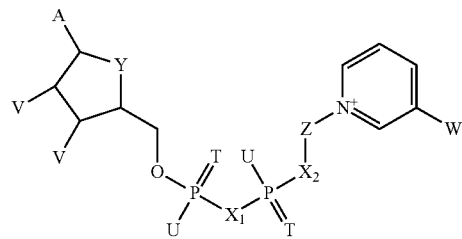

in which
A=adenine,
T=in each case denotes O,
U=in each case denotes OH,
V=in each case denotes OH,
W=$CON(R)_2$ in which R denotes H,
$X_1$=O,
$X_2$=O,
Y=O, and
Z=a carbocyclic 5-membered ring of the general formula (II)

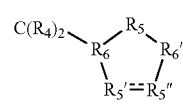

in which a single bond is present between R5' and R5", and in which
R4=H,
R5'=CHOH,
R5"=CHOH,
R5=CR4$_2$,
R6=CH, and
R6'=CH.
In yet another further aspect, the coenzyme is a compound according to formula (I)

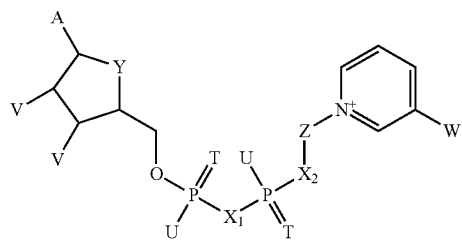

in which
A=adenine,
T=in each case denotes O,
U=in each case denotes OH,
V=in a first case denotes OH and in a second case denotes a phosphate group,
W=CON(R)$_2$ in which R denotes H,
X$_1$=O,
X$_2$=O,
Y=O, and
Z=a carbocyclic 5-membered ring of the general formula (II)

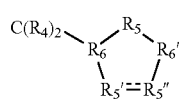

in which a single bond is present between R5' and R5", and in which
R4=H,
R5'=CHOH,
R5"=CHOH,
R5=CR4$_2$,
R6=CH, and
R6'=CH.
In still another further aspect, the coenzyme is thio-NAD. In another further aspect, the coenzyme is thio-NADP.

In a further form of this embodiment, the test element includes a first reagent material which includes the first enzyme or the substrate for the first enzyme, and the coenzyme selected from the group consisting of thio-NAD, thio-NADP and the compound according to formula (I) or a salt or optionally a reduced form thereof. In one aspect of this form, the test element also includes a second reagent material which includes the second enzyme or the substrate for the second enzyme, and a coenzyme selected from the group consisting of FAD, NAD, NADP and the compound according to formula (I) or a salt or optionally a reduced form thereof. In a further aspect, the test element includes a test strip configured to carry the first and second reagent materials. In yet another further aspect, the test strip includes a first electrode system associated with the first reagent material and a second electrode system associated with the second reagent material. In another aspect of this form, the first reagent material further includes one of nitrosoaniline, potassium ferricyanide, and a combination of a phenazine derivative and hexaammineruthenium chloride.

In another embodiment, a reagent material includes 3-hydroxybutyrate dehydrogenase and a coenzyme compound according to formula (I):

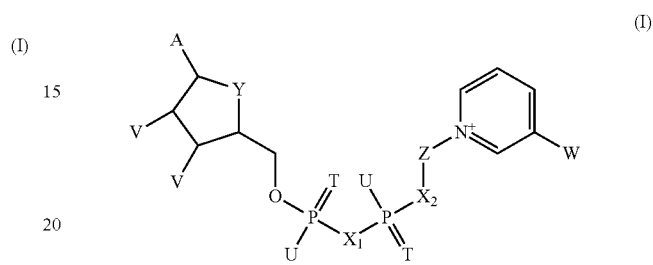

in which
A=adenine or an analog thereof,
T=in each case independently denotes O or S,
U=in each case independently denotes OH, SH, BH$_3^-$, or BCNH$_2^-$,
V=in each case independently denotes OH or a phosphate group,
W=COOR, CON(R)$_2$, COR, or CSN(R)$_2$ in which R in each case independently denotes H or C$_1$-C$_2$-alkyl,
X$_1$, X$_2$=in each case independently denote O, CH$_2$, CHCH$_3$, C(CH$_3$)$_2$, NH, or NCH$_3$,
Y=NH, S, O, or CH$_2$,
Z=a residue comprising a cyclic group with 5 C atoms which optionally contains a heteroatom selected from O, S and N and optionally one or more substituents, and a residue CR4$_2$ wherein CR4$_2$ is bound to the cyclic group and to X$_2$, and
where R4=in each case independently denotes H, F, Cl, or CH$_3$, provided that Z and the pyridine residue are not linked by a glycosidic bond,
or a salt or optionally a reduced form thereof.

In one form of this embodiment, the coenzyme compound is according to formula (I)

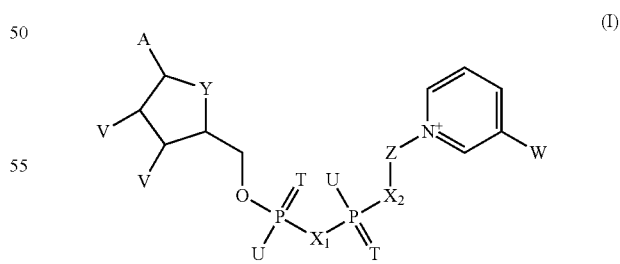

in which
A=adenine,
T=in each case denotes O,
U=in each case denotes OH,
V=in each case denotes OH,
W=CON(R)$_2$ in which R denotes H,
X$_1$=O, $X_2$=O,
Y=O, and
Z=a saturated carbocyclic 5-membered ring of the general formula (II)

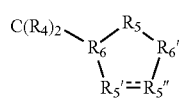
(II)

in which a single bond is present between R5' and R5", and in which
R4=H,
R5'=CHOH,
R5"=CHOH,
R5=CR4$_2$,
R6=CH, and
R6'=CH.

In another form of this embodiment, the coenzyme compound is according to formula (I)

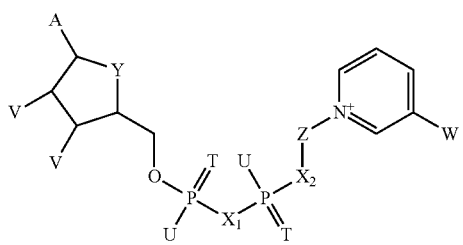
(I)

in which
A=adenine,
T=in each case denotes O,
U=in each case denotes OH,
V=in a first case denotes OH and in a second case denotes a phosphate group,
W=CON(R)$_2$ in which R denotes H,
$X_1$=O,
$X_2$=O,
Y=O, and
Z=a saturated carbocyclic 5-membered ring of the general formula (II)

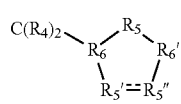
(II)

in which a single bond is present between R5' and R5", and in which
R4=H,
R5'=CHOH,
R5"=CHOH,
R5=CR4$_2$,
R6=CH, and
R6'=CH.

In a further form, the reagent material further includes one of nitrosoaniline, potassium ferricyanide, and a combination of a phenazine derivative and hexaammineruthenium chloride.

In another form of this embodiment, a test element includes a test strip carrying the reagent material for determining a first analyte. In one aspect of this form, the test strip further carries a second reagent material for determining a second analyte. In a further aspect, the second reagent material includes a dehydrogenase enzyme selected from the group consisting of glucose dehydrogenase, lactate dehydrogenase, malate dehydrogenase, glycerol dehydrogenase, alcohol dehydrogenase, sorbitol dehydrogenase, and an amino acid dehydrogenase comprising L-amino acid dehydrogenase. In yet another further aspect, the second reagent material includes a coenzyme selected from the group consisting of FAD, NAD, NADP and a compound according to formula (I):

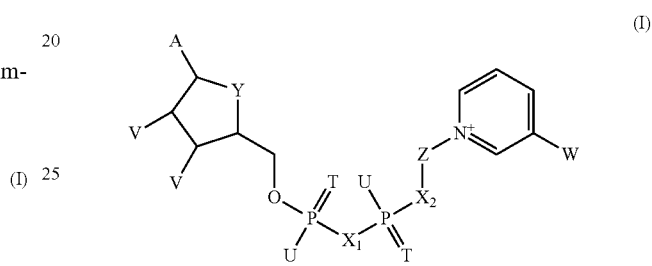
(I)

in which
A=adenine or an analog thereof,
T=in each case independently denotes O or S,
U=in each case independently denotes OH, SH, BH$_3^-$, or BCNH$_2^-$,
V=in each case independently denotes OH or a phosphate group,
W=COOR, CON(R)$_2$, COR, or CSN(R)$_2$ in which R in each case independently denotes H or C$_1$-C$_2$-alkyl,
$X_1$, $X_2$=in each case independently denote O, CH$_2$, CHCH$_3$, C(CH$_3$)$_2$, NH, or NCH$_3$,
Y=NH, S, O, or CH$_2$,
Z=a residue comprising a cyclic group with 5 C atoms which optionally contains a heteroatom selected from O, S and N and optionally one or more substituents, and a residue CR4$_2$ wherein CR4$_2$ is bound to the cyclic group and to X2, and
where R4=in each case independently denotes H, F, Cl, or CH$_3$, provided that Z and the pyridine residue are not linked by a glycosidic bond,
or a salt or optionally a reduced form thereof.

In still another further aspect, the test strip is configured for electrochemical determination of the first and second analytes.

In yet another embodiment, a method for determining first and second analytes in a sample includes providing a test element configured for determining first and second analytes and that includes a first coenzyme-dependent enzyme or a substrate for the first enzyme, a second coenzyme-dependent enzyme or a substrate for the second enzyme, and a coenzyme selected from the group consisting of thio-NAD, thio-NADP, and a compound according to formula (I):

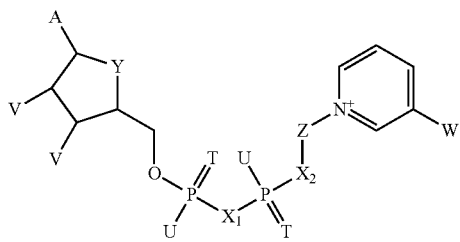

(I)

in which
A=adenine or an analog thereof,
T=in each case independently denotes O or S,
U=in each case independently denotes OH, SH, $BH_3^-$, or $BCNH_2^-$,
V=in each case independently denotes OH or a phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
where R4=in each case independently denotes H, F, Cl, or $CH_3$, provided that Z and the pyridine residue are not linked by a glycosidic bond,
or a salt or optionally a reduced form thereof;
contacting the test element with the sample; detecting the first analyte; and detecting the second analyte.

In one form of this embodiment, the first analyte is hydroxybutyrate and the second analyte is glucose. In one aspect of this form, the steps of detecting the first analyte and detecting the second analyte are performed simultaneously. In another aspect of this form, the steps of detecting the first analyte and detecting the second analyte are completed within five seconds after contacting the test element with the sample.

In yet another embodiment, a method includes the steps of providing a test element configured for determining glucose and ketone values in a sample; contacting the test element with the sample; and determining the glucose and ketone values in the sample within 7.5 seconds after contacting the test element with the sample. In one form, the test element includes a first reagent material for determining the glucose value and a second reagent material for determining the ketone value. In one aspect of this form, the second reagent material includes a hydroxybutyrate dehydrogenase. In another form, the step of determining glucose and ketone values in the sample is completed within 5 seconds after contacting the test element with the sample. In yet another form, the glucose and ketone values are determined within 2 seconds of one another during the determining step. In still another form, the sample comprises blood.

In one form of this method, the test element includes a first coenzyme-dependent enzyme or a substrate for the first enzyme and a second coenzyme-dependent enzyme or a substrate for the second enzyme. The test element also includes a coenzyme selected from the group consisting of thio-NAD, thio-NADP, and a compound according to formula (I):

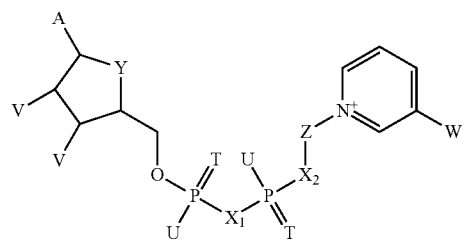

(I)

in which
A=adenine or an analog thereof,
T=in each case independently denotes O or S,
U=in each case independently denotes OH, SH, $BH_3^-$, or $BCNH_2^-$,
V=in each case independently denotes OH or a phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
where R4=in each case independently denotes H, F, Cl, or $CH_3$, provided that Z and the pyridine residue are not linked by a glycosidic bond,
or a salt or optionally a reduced form thereof.

In one aspect, the first analyte is hydroxybutyrate and the first enzyme is a hydroxybutyrate dehydrogenase. In a further aspect, the hydroxybutyrate dehydrogenase is 3-hydroxybutyrate dehydrogenase. In a further aspect, the second enzyme is a dehydrogenase selected from the group consisting of glucose dehydrogenase, lactate dehydrogenase, malate dehydrogenase, glycerol dehydrogenase, alcohol dehydrogenase, sorbitol dehydrogenase, and an amino acid dehydrogenase comprising L-amino acid dehydrogenase. In still another aspect, the second analyte is glucose and the second enzyme is a glucose dehydrogenase or a glucose oxidase. In a further aspect, the coenzyme is a compound according to formula (I)

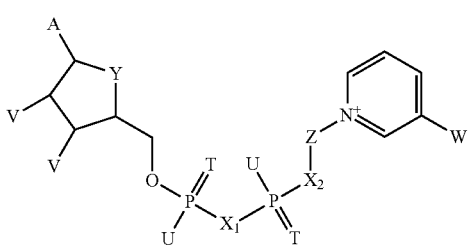

(I)

in which
A=adenine,
T=in each case denotes O,
U=in each case denotes OH,
V=in each case denotes OH,
W=$CON(R)_2$ in which R denotes H,
$X_1$=O, $X_2=O$,
$Y=O$, and
Z=a carbocyclic 5-membered ring of the general formula (II)

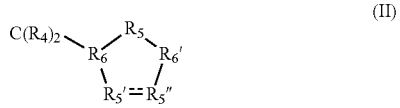 (II)

in which a single bond is present between R5' and R5", and in which
R4=H,
R5'=CHOH,
R5"=CHOH,
R5=CR4$_2$,
R6=CH, and
R6'=CH.
In yet another further aspect, the coenzyme is a compound according to formula (I)

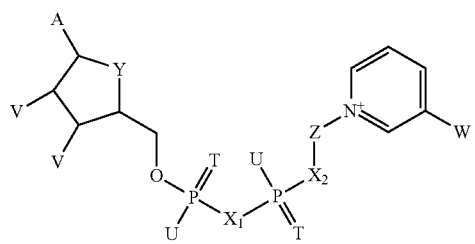 (I)

in which
A=adenine,
T=in each case denotes O,
U=in each case denotes OH,
V=in a first case denotes OH and in a second case denotes a phosphate group,
W=CON(R)$_2$ in which R denotes H,
$X_1=O$,
$X_2=O$,
$Y=O$, and
Z=a carbocyclic 5-membered ring of the general formula (II)

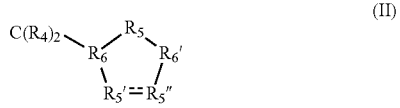 (II)

in which a single bond is present between R5' and R5", and in which
R4=H,
R5'=CHOH,
R5"=CHOH,
R5=CR4$_2$,
R6=CH, and
R6'=CH.
In still another further aspect, the coenzyme is thio-NAD. In another further aspect, the coenzyme is thio-NADP.

In a further aspect, the test element includes a first reagent material which includes the first enzyme or the substrate for the first enzyme, and the coenzyme selected from the group consisting of thio-NAD, thio-NADP and the compound according to formula (I) or a salt or optionally a reduced form thereof. In a further aspect, the test element also includes a second reagent material which includes the second enzyme or the substrate for the second enzyme, and a coenzyme selected from the group consisting of FAD, NAD, NADP and the compound according to formula (I) or a salt or optionally a reduced form thereof. In a further aspect, the test element includes a test strip configured to carry the first and second reagent materials. In yet another further aspect, the test strip includes a first electrode system associated with the first reagent material and a second electrode system associated with the second reagent material. In another aspect, the first reagent material further includes one of nitrosoaniline, potassium ferricyanide, and a combination of a phenazine derivative and hexaammineruthenium chloride.

Another aspect of the present application is a unique technique for measuring the presence and/or concentration of multiple analytes in test samples. Other aspects include unique methods, systems, devices, kits, assemblies, equipment, and/or apparatus related to analyte detection in a sample.

Further aspects, embodiments, forms, features, benefits, objects, and advantages shall become apparent from the detailed description and figures provided herewith.

DETAILED DESCRIPTION OF THE ILLUSTRATED EMBODIMENTS

Figure 1:
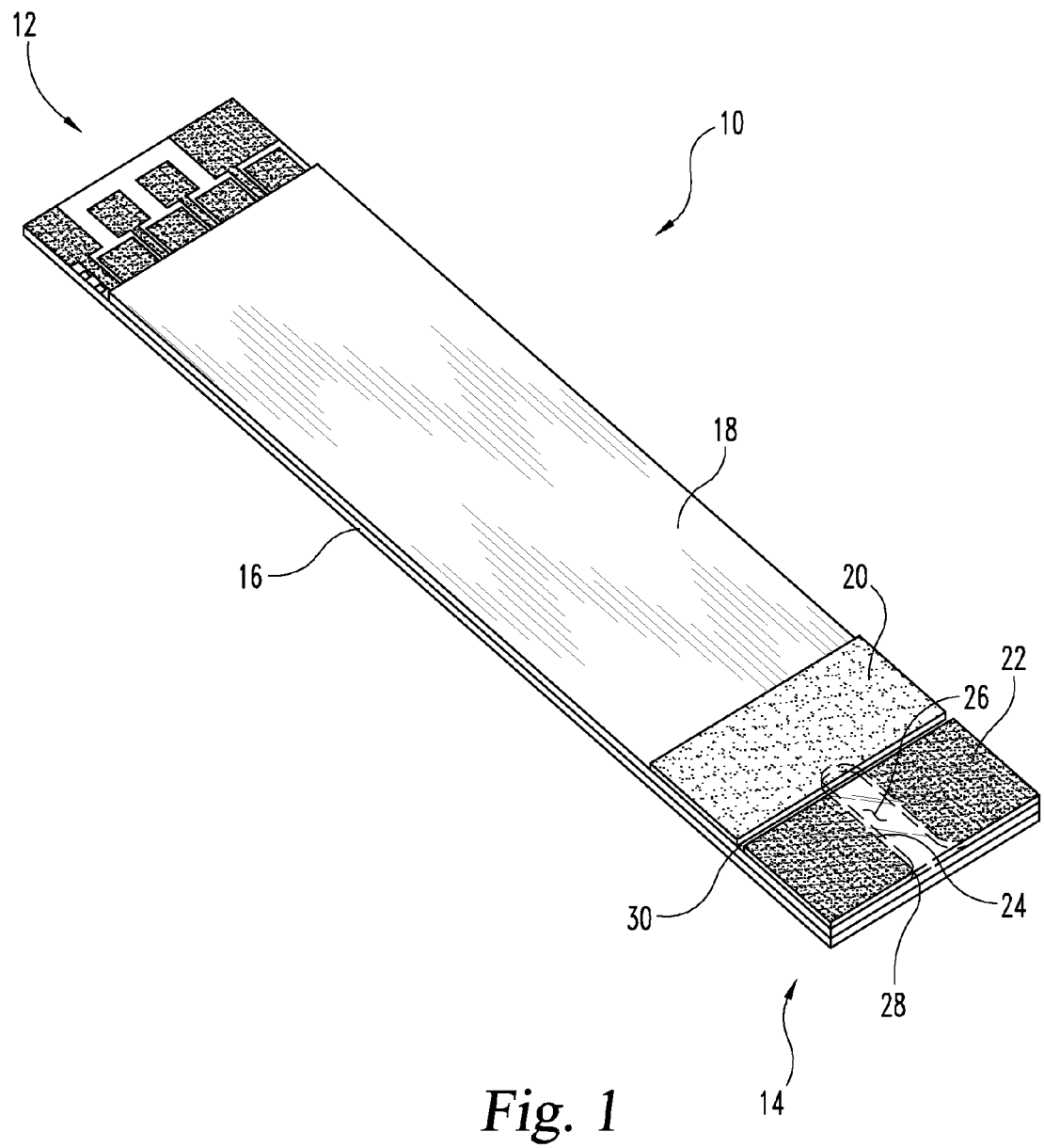
FIG. 1 is a perspective view of a first embodiment test element.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Reagent materials and associated test elements are provided. In one embodiment, a dual function test element includes a first coenzyme-dependent enzyme or a substrate for the first enzyme, a second coenzyme-dependent enzyme or a substrate for the second enzyme, and a coenzyme selected from the group consisting of thio-NAD, thio-NADP, and a compound according to formula (I). In one aspect, the first analyte is hydroxybutyrate and the first enzyme is a hydroxybutyrate dehydrogenase, and the second analyte is glucose and the second enzyme is a glucose dehydrogenase or a glucose oxidase. In another embodiment, the test element is part of a system that also includes a meter configured to interact with the test element to assess first and second analytes in a sample. This assessment may range from detecting the presence of the first and second analytes to determining the concentration of the first and second analytes. The first and second analytes and the sample fluid may be any for which the test system is appropriate, although in one particular but non-limiting form the first analyte is hydroxybutyrate, the second analyte is glucose, and the sample fluid is blood or interstitial fluid. Other aspects of the subject application are directed to unique reagent materials. Further aspects and features of the present application are described with respect to the illustrated embodiments as follows.

Figure 2:
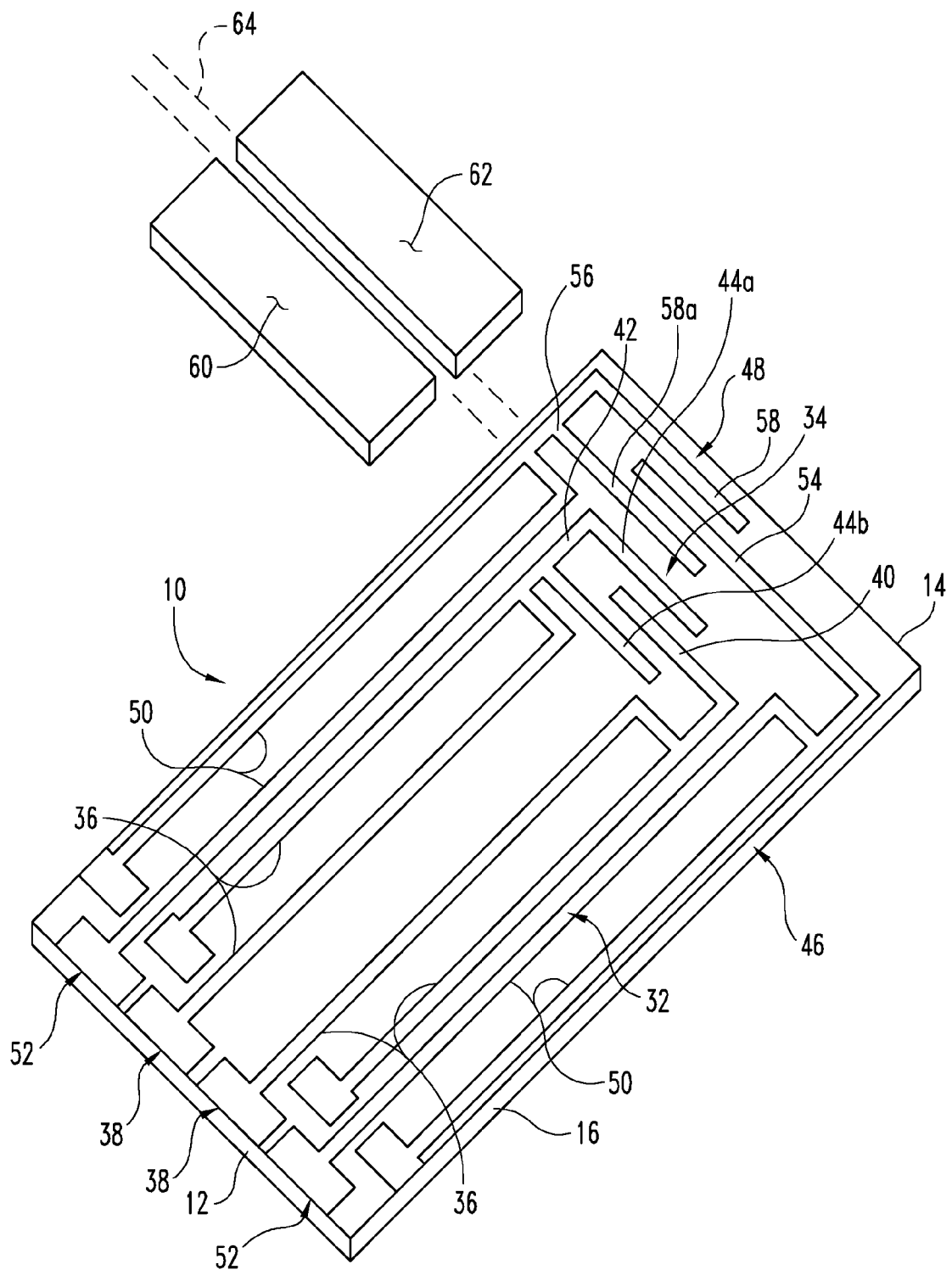
FIG. 2 is an exploded, perspective view of various features of the test element of FIG. 1.

Referring to FIGS. 1 and 2, further details of a first embodiment test element 10 configured for assessing first and second analytes in a sample will now be provided. Test element 10 is provided as an electrochemical sensor including a sample-receiving chamber for the sample fluid, and first and second reagent materials for producing electrochemical signals in the presence of the first and second analytes. In the illustrated form, test element 10 extends between a meter insertion end 12 and a dosing end 14. In one non-illustrated form, the shape of dosing end 14 may be distinguishable from meter insertion end 12 so as to aid users in proper handling and use of test element 10. Test element 10 may also include one or more graphics (not shown) to provide a user guidance on proper handling and use.

Test element 10 is provided in the form of a disposable test strip which has a laminar construction including a base substrate 16, a spacing layer 18, a body cover 20 and a chamber cover 22. Further details of test elements including a similar laminar construction are provided in U.S. Pat. No. 7,727,467, the contents of which are incorporated herein by reference in their entirety. Spacing layer 18 includes a void portion 24 to provide a sample-receiving chamber 26 extending between base substrate 16 and body cover 20 and chamber cover 22. In this configuration, sample-receiving chamber 26 opens at dosing end 14 of test element 10 through an opening 28 which is configured to facilitate passage of a sample fluid into sample-receiving chamber 26. Forms in which sample-receiving chamber 26 opens through an opening positioned along a side of test element 10 are also contemplated. Forms in which the sample-receiving chamber 26 opens through an opening positioned along the full length of the dosing end 14 and including a portion of the sides are also contemplated.

Body cover 20 and chamber cover 22 overly spacing layer 18 and define a slot 30 therebetween which provides a vent opening communicating with sample-receiving chamber 26 to allow air to escape sample-receiving chamber 26 as a sample fluid enters sample-receiving chamber 26 through opening 28. Slot 30 is located at a position relative to sample-receiving chamber 26 that is interior of the location of the electrode systems (described below) positioned in sample-receiving chamber 26. Sample fluid entering sample-receiving chamber 26 will progress as far as the vent opening, but no further. When viewed from the top, the slot provides a visual indication of a "fill-line" to confirm that the electrode systems in sample-receiving chamber 26 have been properly wetted or covered to function properly. Additionally or alternatively, dose sufficiency electrodes may also be positioned adjacent slot 30 to detect when the sample fluid has progressed to slot 30 to assure that wetting of the measuring electrodes has occurred.

Other than the electrode systems and reagent materials, sample-receiving chamber 26 may be empty or may alternatively include a sorbent material. Suitable sorbent materials include polyester, nylon, cellulose, and cellulose derivatives such as nitrocellulose. When included, a sorbent material helps facilitate uptake of the sample fluid by assisting in wicking the fluid into sample-receiving chamber 26. The use of a sorbent material would also serve to further reduce the void volume of sample-receiving chamber 26 for reception of the sample fluid. In one form, the filling of sample-receiving chamber 26 occurs by capillary action. The filling of sample-receiving chamber 26 can also be augmented by other means, such as by applying a pressure on the sample fluid to push it into sample-receiving chamber 26, and/or creating a vacuum on sample-receiving chamber 26 to pull the sample fluid into sample-receiving chamber 26. In addition, one or more surfaces of sample-receiving chamber 26 can be formed from a hydrophilic material, provided with a coating of a hydrophilic material, or subjected to a hydrophilicity increasing treatment in order to facilitate filling of sample-receiving chamber 26 with the test sample.

Test element 10 is configured to detect the presence of, and/or measure the concentration of, first and second analytes by way of electrochemical oxidation and reduction reactions. These reactions are transduced to an electrical signal that can be correlated to an amount or concentration of the analyte. As shown in FIG. 2, where only some features of test element 10 are illustrated, substrate 16 carries a first electrode system 32 that includes a plurality of electrodes 34 and electrode traces 36 terminating in contact pads 38. Electrodes 34 are defined as those portions of electrode traces 36 that are positioned within sample-receiving chamber 26. Substrate 16 also carries a second electrode system 46 that includes a plurality of electrodes 48 and electrode traces 50 terminating in contact pads 52. Electrodes 48 are defined as those portions of electrode traces 50 that are positioned within sample-receiving chamber 26. It should be understood that the illustrated configurations of electrode systems 32, 46 are not limiting, and that alternative configurations are contemplated.

Test element 10 also includes a first reagent material 60 which overlies at least a portion of electrodes 34 of first electrode system 32 within sample-receiving chamber 26, and a second reagent material 62 which overlies at least a portion of electrodes 48 of second electrode system 46 within sample-receiving chamber 26. First and second reagent materials 60, 62 are suitable for producing electrochemical signals in the presence of respective first and second test analytes, and are disposed within sample-receiving chamber 26 in position to provide the electrochemical signal to electrodes 34, 48 in sample-receiving chamber 26. In the illustrated form, a space 64 extends between first and second reagent materials 60, 62, although forms in which space 64 is absent and first and second reagent materials form a continuous layer over electrodes 34, 48 are also contemplated. Further details regarding first and second reagent materials 60, 62 will be provided herein below.

Electrodes 34 of first electrode system 32 include a set of measuring electrodes in the form of working electrode 40 and counter electrode 42 which includes portions 44a and 44b spaced on opposite sides of working electrode 40. As used herein, a "working electrode" is an electrode at which an analyte is electrooxidized or electroreduced with or without the agency of a redox mediator, while the term "counter electrode" refers to an electrode that is paired with the working electrode and through which passes an electrochemical current equal in magnitude and opposite in sign to the current passed through the working electrode. The term "counter electrode" is meant to include counter electrodes which also function as reference electrodes (i.e., counter/reference electrodes). Electrodes 48 of second electrode system 46 include a set of measuring electrodes in the form of working electrode 54 and counter electrode 56 which includes portions 58a and 58b spaced on opposite sides of working electrode 54. In this arrangement, sample-receiving chamber 26 is configured such that sample fluid entering sample-receiving chamber 26 is placed in electrolytic contact with working electrodes 40 and 54 and counter electrodes 42 and 56. This arrangement also allows electrical current to flow between the measuring electrodes to affect the electrooxidation or electroreduction of the first and second analytes. It should be appreciated however that the foregoing is only one of a number of configurations for the measuring electrodes.

Figure 3:
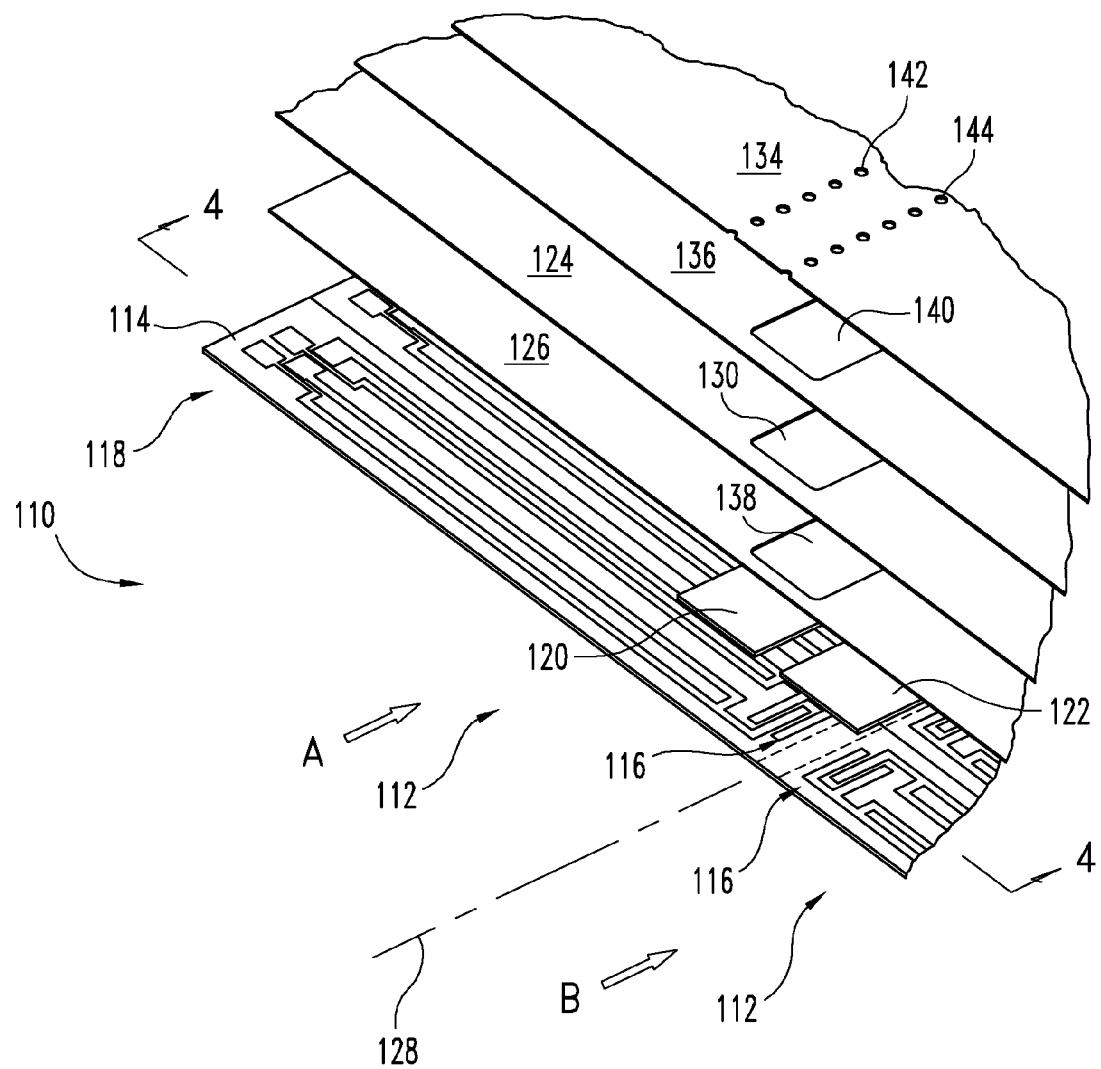
FIG. 3 is an exploded, perspective view of a second embodiment test element.
Figure 4:
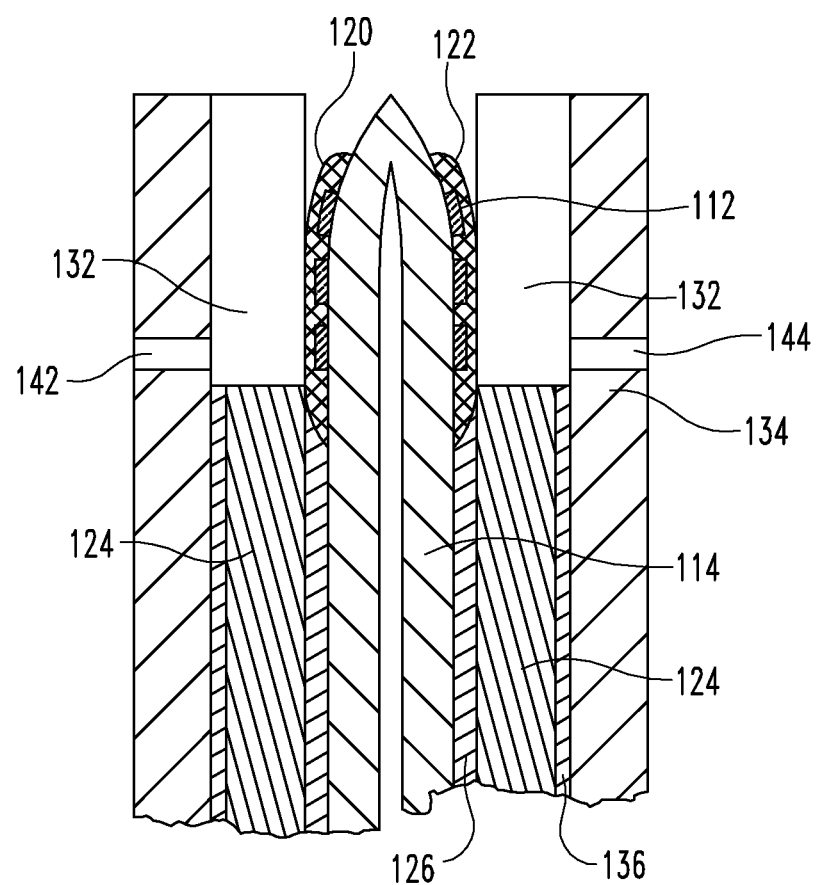
FIG. 4 is a fragmentary, sectional view of the test element of FIG. 3.
Figure 5:
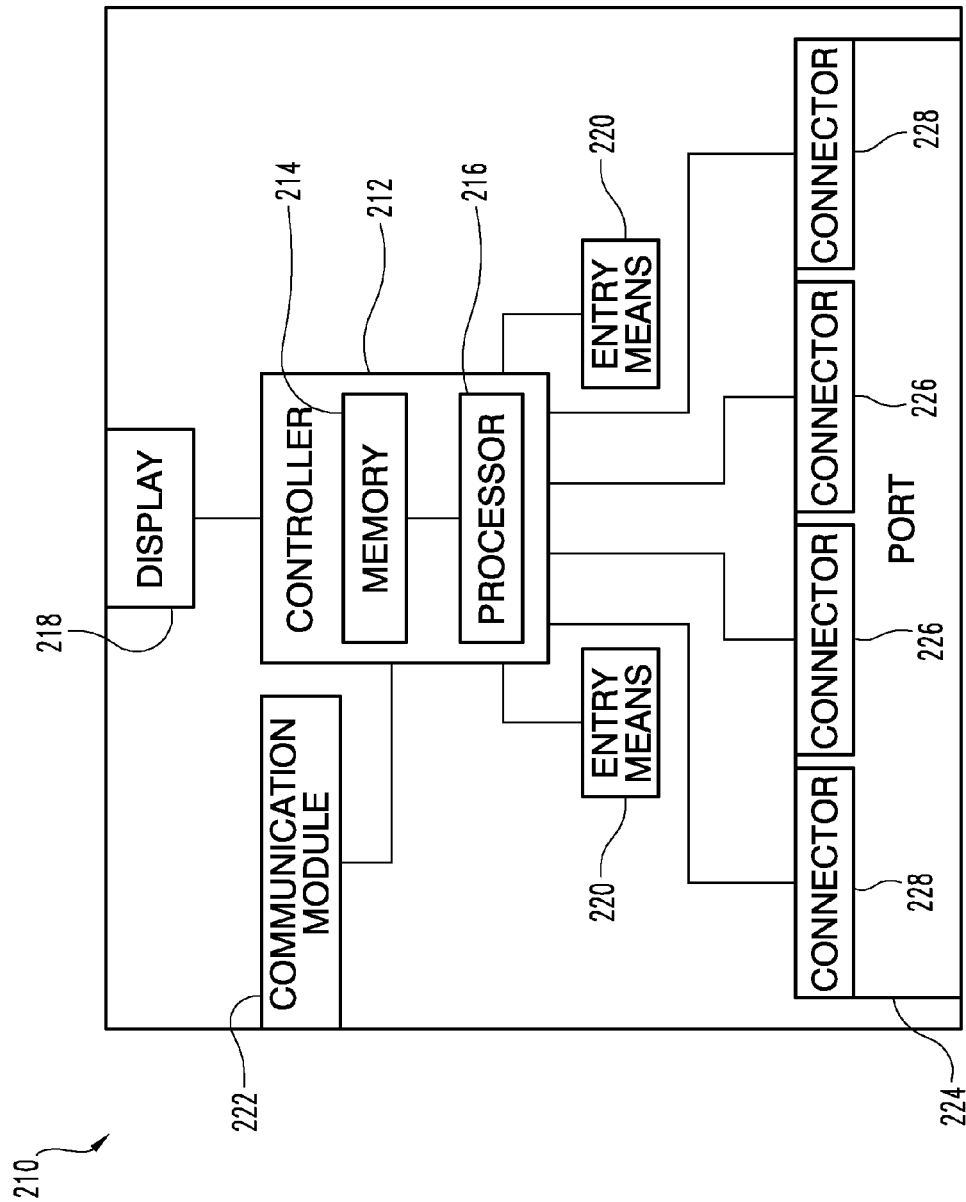
FIG. 5 is a schematic illustration of an analytical instrument structured for use with the test element of FIG. 1.

An alternative embodiment test element 110 for assessing first and second analytes in a sample is illustrated in FIGS. 3 and 4. Test element 110 is produced utilizing a head to head manufacturing technique. Further details of this technique, and of test element 110 generally, are found in International Patent Publication No. WO 2012/003306, the contents of which are incorporated herein by reference in their entirety. As illustrated in FIG. 3, electrode patterns 112 are arranged in two columns (one set of electrode patterns in column A and one set in column B) on an elongated layer (tape) of a substrate 114. Test element 110 also includes sample chamber electrode patterns 116 located near each other and near the center of substrate 114 and contact pads 118 spaced apart from one another and located near the opposite edges of substrate 114. In the illustrated form, the electrode patterns are all similar; however in alternative forms at least some of the electrode patterns may be different from other electrode patterns. A first reagent material 120 is applied over the sample chamber electrodes 116 in column A and a second reagent material 122 is applied over the sample chamber electrodes 116 in column B.

A spacer layer 124 is attached to the top of substrate 114 with an adhesive layer 126. In the illustrated form, one elongated strip or tape forms spacer layer 124 to cover the electrode patterns of both columns A and B, although forms in which two separate strips of spacer layer 124 are individually attached to substrate 114 in column A and column B and aligned along centerline 128 are also possible. Spacer layer 124 includes a plurality of cutout portions 130 arranged along centerline 128. When spacer layer 124 is assembled with substrate 114, cutout portions 130 will form the perimeters of sample chambers 132 (FIG. 4). A single, continuous upper substrate layer 134 is attached to the top of spacer layer 124 with an adhesive layer 136 and includes a plurality of vent openings 142, 144 to facilitate venting of sample chambers 132 as they are filled with a sample fluid. While not previously discussed, it should be appreciated that adhesive layers 126, 136 include a plurality of cutout portions 138, 140, respectively, arranged along centerline 128 and corresponding to cutout portions 130 of spacer layer 124. Alternatively, it is contemplated that adhesive layer 136 may be a solid layer without any openings or cutouts.

After substrate 114, reagent materials 120, 122, spacer layer 124 and upper substrate 134 are combined and laminated together, the sheet or roll is separated such that electrodes patterns 116 in columns A and B remain attached to one another while the test strips in adjacent rows (side-by-side oriented test strips) are separated. In other words, the test strips in column A are not fully separated from the test strips in column B, and test strip pairs are formed with each pair of test strips arranged in a head-to-head manner. Each test strip pair may be folded to place contact pads 118 of the test strip from column A adjacent contact pads 118 of the test strip from column B, and to place the sampling end of the test strip from column A adjacent to and facing the same direction as the sampling end of the test strip from column B. Using this type of head-to-head test strip pair, a dual-use biosensor is provided in which a user can apply a sample of bodily fluid to both test strips simultaneously in order to test for first and second different analytes using a single sample. In one embodiment, a blood filtering media may be provided within dual sample chambers 132 prior to folding the pair together in order to prevent blood and reagent mixing between chambers 132.

It should be appreciated that chambers 132 in each of the head-to-head oriented pair of test strips should be exposed when the pair of test strips are bent along centerline 128. Alternative manufacturing techniques can be used to ensure both sample chambers 132 are exposed. For example, in one embodiment, one of the substrate layers, e.g. top layer 134, is fully separated along centerline 128 during manufacture while the substrate 114 is either unmodified or modified to predictably bend about centerline 128. In an alternative embodiment, one of the substrate layers is modified, such as through perforations or partial cutting to be easily separated by the user along centerline 128 while the other substrate is modified, such as by scoring, denting or crimping, to predictably bend or separate about a straight line, for example, centerline 128. In still another embodiment, both top layer 134 and lower substrate 114 are modified to allow the head-to-head test strips to be folded in either direction, i.e., the user may choose to bend the head-to-head pair of test strips to have top layers 134 of the two test strips positioned adjacent one another or to have substrates 114 of the two test strips positioned adjacent one another.

Substrates 16, 114 may be formed of an insulating material on which electrode systems 32, 46 and electrode patterns 112, respectively, are positioned. Typically, plastics such as vinyl polymers, polyimides, polyesters, and styrenes provide the electrical and structural properties which are required. Further, because the test elements can be mass producible from rolls of material, it is desirable that the material properties be appropriate to have sufficient flexibility for roll processing, while also giving a useful stiffness to the finished element. The material for substrates 16, 114 can be selected as a flexible polymeric material such as polyester, including high temperature polyester materials; polyethylene naphthalate (PEN); and polyimide, or mixtures of two or more of these. Polyimides are available commercially, for example under the trade name Kapton®, from E.I. duPont de Nemours and Company of Wilmington, Del. (duPont). One specific material possible for substrates 16, 114 is MELINEX® 329 available from duPont.

The working and counter electrodes, and the remaining portions of the electrode systems 32, 46 and electrode patterns 112, may be formed from a variety of materials. In one aspect, the electrodes should have a relatively low electrical resistance and should be electrochemically inert over the operating range of the test elements. Suitable conductors for the working electrode include gold, palladium, platinum, carbon, titanium, ruthenium dioxide, and indium tin oxide, and iridium, as well as others. The counter electrode may be made of the same or different materials, e.g., silver/silver chloride. In one specific embodiment, the working and counter electrodes are both gold electrodes.

Electrode systems 32, 46 and electrode patterns 112 may be applied to substrates 16, 114, respectively, in any fashion that yields electrodes of adequate conductivity and integrity. Exemplary processes include sputtering and printing, just to provide a few non-limiting possibilities. In one specific form, gold electrodes are provided by coating the materials of substrates 16, 114 and then removing selected portions of the coating to yield the electrode systems 32, 46 and electrode patterns 112. One particular method for removing portions of the coating include laser ablation, and more particularly broad field laser ablation, as disclosed in U.S. Pat. No. 7,073, 246, the contents of which are incorporated herein by reference in their entirety.

Laser ablative techniques typically include ablating a single metallic layer or a multi-layer composition that includes an insulating material and a conductive material, e.g., a metallic-laminate of a metal layer coated on or laminated to an insulating material. The metallic layer may contain pure metals, alloys, or other materials, which are metallic conductors. Examples of metals or metallic-like conductors include: aluminum, carbon (such as graphite), cobalt, copper, gallium, gold, indium, nickel, palladium, platinum, silver, titanium, mixtures thereof, and alloys or solid solutions of these materials. In one aspect, the materials are selected to be essentially unreactive to biological systems, non-limiting examples of which include gold, platinum, palladium, carbon and iridium tin oxide. The metallic layer may be any desired thickness which, in one particular form, is about 500 nm.

It should be understood that the illustrated form of test elements 10, 110 is not-limiting, and that alternative configurations for the dual function test elements of the subject application, including those arranged for optical detection techniques, are also contemplated. In this regard, in one additional and non-limiting form a dual function test element may include a sandwich-type of configuration where a first substrate that carries a first electrode system is positioned over a second substrate that carries a second electrode system. The first and second substrates are spaced apart from one another by an intermediate layer that includes a capillary channel or a capillary channel is otherwise formed between the first and second substrates. In this configuration, sample fluid that enters into the capillary channel is directed toward the first and second electrode systems such that simultaneous or near simultaneous covering of the first and second electrode systems occurs. While not previously discussed, it should be further understood that the first substrate is provided with a first reagent material suited for determination of a first analyte and that the second substrate is provided with a second reagent material suited for determination of a second analyte. By way of non-limiting example, one technique for producing test elements having this configuration involves separately producing the first substrate carrying the first reagent material and the first electrode system and the second substrate carrying the second reagent material and the second electrode system and then assembling the first and second substrates together.

In another non-limiting form, a dual function test element may include a slightly different sandwich-type of configuration. In this configuration, a first substrate that carries a first electrode system is positioned over a second substrate that carries a second electrode system. However, the first and second substrates are joined by an adhesive layer and each includes a separate sample chamber positioned over its respective electrode system in lieu of a single capillary channel. In this form, the test element includes a configuration that facilitates simultaneous or near simultaneous filling of the individual sample chambers such that simultaneous or near simultaneous covering of the first and second electrode systems also occurs. While not previously discussed, it should be further understood that the first substrate is provided with a first reagent material suited for determination of a first analyte and that the second substrate is provided with a second reagent material suited for determination of a second analyte. This test element may also be produced utilizing the technique discussed above in connection with the other sandwich-type of configuration described herein. Further details of one non-limiting test element having this form are provided in International Patent Publication No. WO 2012/003306 (incorporated herein above).

Further examples of non-limiting arrangements that may be utilized for the test element of the subject application are disclosed in U.S. Pat. Nos. 6,984,307 and 4,397,956, the contents of which are incorporated herein by reference in their entirety.

It is contemplated that test elements 10, 110 may be useful for the determination of a wide variety of first and second analytes from a biological fluid. For example, test elements 10, 110 may be readily adapted for use with reagent materials 60, 62 and 120, 122 having any suitable chemistry that can be used to assess the presence and/or concentration of the first and second analytes. Reagent materials 60, 62 and 120, 122 are operable for reacting with the first and second analytes to produce the electrochemical signals that represent the presence and/or concentration of the first and second analytes in the sample fluid. As will be discussed in greater detail below, reagent materials 60, 62 and 120, 122 can include a variety of active components selected to determine the presence and/or concentration of various first and second analytes. The test chemistries of reagent materials 60, 62 and 120, 122 are therefore selected in respect to the first and second analytes to be assessed. Such analytes may include, for example, glucose, cholesterol, HDL cholesterol, triglycerides, glycerine, lactates, lactate dehydrogenase, malates, alcohol, uric acid, sorbitol, amino acids, 1,5-anhydroglucitol and analytes representative of ketone bodies, such as hydroxybutyrate. In one particular embodiment, test elements 10, 110 include reagent materials 60, 62 and 120, 122, respectively, which are selected to determine the presence and/or concentration of hydroxybutyrate and glucose in blood.

Non-limiting examples of biological fluids in which the first and second analytes can be assessed include any bodily fluid in which the analytes can be measured, such as interstitial fluid, tears, urine, and blood. The term "blood" in the context of this document includes whole blood and its cell-free components, namely plasma and serum. When the test elements are configured for the testing of hydroxybutyrate and glucose, the sample fluid may specifically include, for example, fresh capillary blood obtained from the finger tip or approved alternate sites (e.g., forearm, palm, ear lobe, upper arm, calf and thigh), fresh venous blood or urine. In addition, the test elements may also be useful in connection with control fluids that are used in conventional fashion to verify the integrity of the system for testing.

The bodily fluid containing the analyte to be assessed may be acquired and delivered to the test elements in any fashion. For example, a blood sample may be obtained in conventional fashion by incising the skin, such as with a lancet, and then contacting the test element with fluid that appears at the skin surface. In one aspect, the test elements are operable for assessing the targeted analyte while only using very small fluid samples. Similarly, in one aspect, only a slight skin incision is necessary to produce the volume of fluid required for the test, and the pain and other concerns with such method can be minimized or eliminated.

Reagent materials 60, 120 include a first coenzyme-dependent enzyme or a substrate for the first enzyme and a suitable coenzyme. These components are typically dissolved or suspended in a matrix. The liquid test sample hydrates or dissolves the matrix, and the first analyte diffuses through the matrix to react with one or more of the active components. Suitable enzymes that could be included in reagent materials 60, 120 are for example dehydrogenases selected from glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1,1,6), alcohol dehydrogenase (E.C.1.1.1.1), hydroxybutyrate dehydrogenase (HBDH), such as 3-hydroxybutyrate dehydrogenase or beta-hydroxybutyrate dehydrogenase, alpha-hydroxybutyrate dehydrogenase and gamma-hydroxybutyrate dehydrogenase, sorbitol dehydrogenase, and amino acid dehydrogenase e.g. L-amino acid dehydrogenase (E.C.1.4.1.5). Further suitable enzymes are oxidases such as glucose oxidase (E.C.1.1.3.4) or cholesterol oxidase (E.C.1.1.3.6) or aminotransferases such as aspartate or alanine aminotransferase, 5'-nucleotidase or creatine kinase. Depending on the selected enzyme, potential coenzymes suitable for use in reagent materials 60, 120 include FAD, NAD, NADP, thio-NAD, thio-NADP, and a compound according to formula (I)

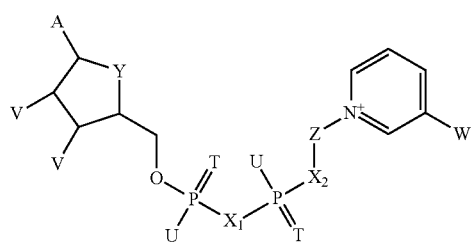

(I)

in which
A=adenine or an analog thereof,
T=in each case independently denotes O or S,
U=in each case independently denotes OH, SH, $BH_3^-$, or $BCNH_2^-$,
V=in each case independently denotes OH or a phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
where R4=in each case independently denotes H, F, Cl, or $CH_3$, provided that Z and the pyridine residue are not linked by a glycosidic bond,
or a salt or optionally a reduced form thereof.
In one embodiment, W=$CONH_2$ or $COCH_3$.

Exemplary substituents on Z are selected from the group consisting of OH, F, Cl, and $C_1$-$C_2$ alky which are optionally fluorinated or chlorinated and/or OH-substituted, O—$C_1$-$C_2$-alkyl.

In another embodiment, a first residue V is OH and a second residue V is a phosphate group. Optionally, the one OH group and the one phosphate group can form a ring together with the carbon atoms to which they are bound.

Non-limiting examples of adenine analogues include $C_8$-substituted and $N_6$-substituted adenine, deaza variants such as 7-deaza aza variants such as 8-aza or combinations such as 7-deaza or 8-aza or carbocyclic analogues such as formycin where the 7-deaza variants can be substituted in the 7 position with halogen, $C_1$-$C_6$-alkinyl, $C_1$-$C_6$-alkenyl or $C_1$-$C_6$-alkyl. In a further embodiment the compounds contain adenosine analogues which contain for example 2-methoxydeoxyribose, 2'-fluorodeoxy-ribose, hexitol, altritol or polycyclic analogues such as bicyclic, LNA and tricyclic sugars instead of ribose. In one form, (di)phosphate oxygens can also be isoelectronically substituted such as for example $O^-$ by $S^-$ and/or by $BH_3^-$, O by NH, $NCH_3$ and/or by $CH_2$ and =O by =S. In one embodiment at least one residue U of a compound according to formula (I) is different from OH and in other embodiments at least one residue U=$BH_3^-$.

Another more particular but non-limiting compound according to formula (I) in which:
A=adenine,
T=in each case denotes O,
U=in each case denotes OH,
V=in each case denotes OH,
W=$CON(R)_2$ in which R denotes H,
$X_1$=O,
$X_2$=O,
Y=O, and
Z=a carbocyclic 5-membered ring of the general formula (II)

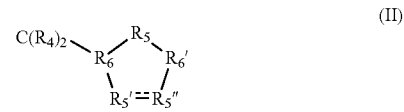

(II)

in which a single bond is present between R5' and R5", and in which
R4=H,
R5'=CHOH,
R5"=CHOH,
R5=$CR4_2$,
R6=CH, and
R6'=CH
is carba-NAD or cNAD.
carba-NAD has the following structure:

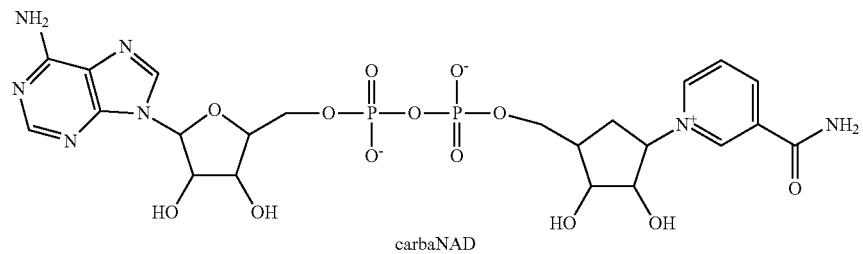 [SMILES: NC(=O)c1ccc[n+](C2CC(COP(=O)([O-])OP(=O)([O-])OCC3OC(n4cnc5c(N)ncnc54)C(O)C3O)C(O)C2O)c1]

carbaNAD

Yet another more particular but non-limiting compound according to formula (I) in which:

A=adenine,
T=in each case denotes O,
U=in each case denotes OH,
V=in a first case denotes OH and in a second case denotes a phosphate group,
W=CON(R)₂ in which R denotes H,
X₁=O,
X₂=O,
Y=O, and
Z=a carbocyclic 5-membered ring of the general formula (II)

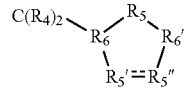
(II)

in which a single bond is present between R5' and R5", and in which
R4=H,
R5'=CHOH,
R5"=CHOH,
R5=CR4₂,
R6=CH, and
R6'=CH
is carba-NADP or cNADP.
carba-NADP has the following structure:

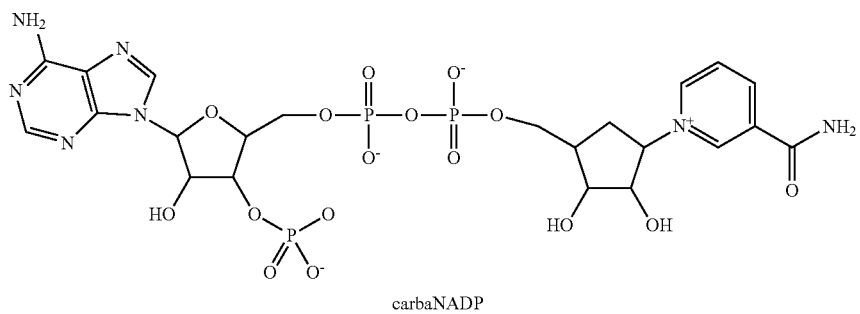 [SMILES: NC(=O)c1ccc[n+](C2CC(COP(=O)([O-])OP(=O)([O-])OCC3OC(n4cnc5c(N)ncnc54)C(O)C3OP(=O)([O-])O)C(O)C2O)c1]

carbaNADP

Other particular but non-limiting compounds according to formula (I) include borano carba-NAD, cyclopentyl NAD, and carba-NAD cyclophosphate. These compounds have the following structures:

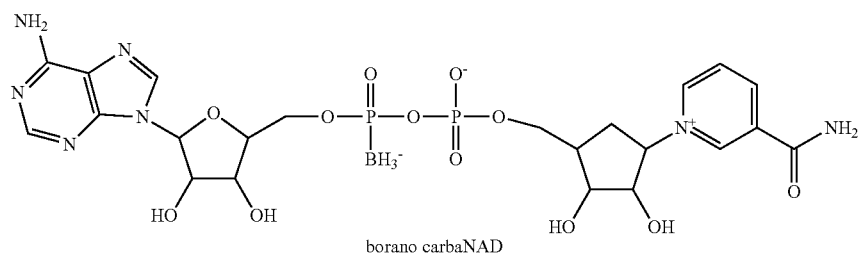

borano carbaNAD

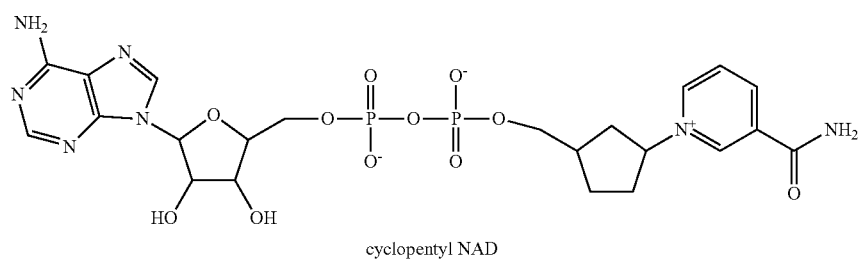

cyclopentyl NAD

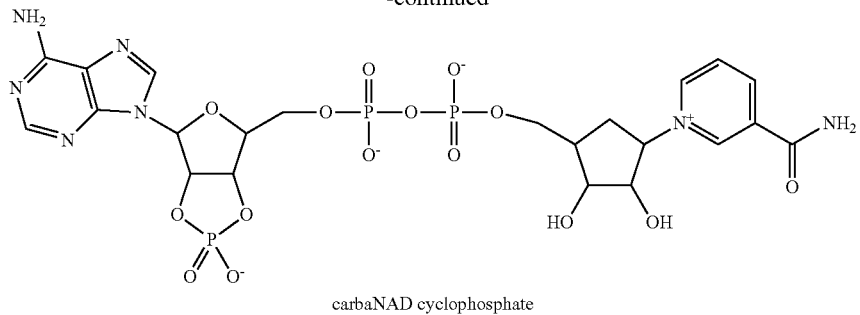

carbaNAD cyclophosphate

Further details regarding compounds according to formula (I) and synthesis of the same are provided in U.S. Patent Publication No. 2008/0231809, the contents of which are incorporated herein by reference in their entirety.

In one embodiment, reagent materials 60, 120 are operable to facilitate detection of the presence and/or concentration of hydroxybutyrate and include a hydroxybutyrate dehydrogenase. Non-limiting examples of hydroxybutyrate dehydrogenase include alpha-hydroxybutyrate dehydrogenase, beta or 3-hydroxybutyrate dehydrogenase, and gamma-hydroxybutyrate dehydrogenase. In one particular form, the hydroxybutyrate dehydrogenase is 3-hydroxybutyrate dehydrogenase. In this embodiment, reagent materials 60, 120 further include a coenzyme selected from thio-NAD, thio-NADP, and a compound according to formula (I) or a salt or optionally a reduced form thereof. In one particular form, reagent materials 60, 120 include 3-hydroxybutyrate dehydrogenase and one of carbaNAD and carbaNADP. In forms where the first reagent material includes a hydroxybutyrate dehydrogenase and a coenzyme selected from thio-NAD, thio-NADP, and a compound according to formula (I) or a salt or optionally a reduced form thereof, it has been surprisingly discovered that detection of the presence and/or concentration of hydroxybutyrate can be completed in or about five seconds after the test element has been contacted with the sample, which generally corresponds to state of the art glucose testing which takes about five seconds. Further details in this regard are provided in connection with the "EXAMPLES" below. It should be understood that the use of reagent materials that require more than five seconds to complete detection of the presence and/or concentration of hydroxybutyrate are also suitable for use in test elements of the subject application.

In addition, while the use of a reagent material that includes a hydroxybutyrate dehydrogenase and a coenzyme selected from thio-NAD, thio-NADP, and a compound according to formula (I) or a salt or optionally a reduced form thereof has been described herein in connection with test elements having dual functionalities, it should be understood that the use of this reagent material in connection with test elements having single functionality is also possible. Non-limiting examples of additional forms of test elements for which use of this reagent material is contemplated are disclosed in U.S. Patent Application Publication No. 2005/0016844 and U.S. Pat. No. 7,008,799, the contents of which are hereby incorporated herein by reference in their entirety. It should also be appreciated that the reagent material does not require any additional enzymes, such as diaphorase, to be operable for the detection of presence and/or concentration of hydroxybutyrate in forms where it includes a hydroxybutyrate dehydrogenase and a coenzyme selected from thio-NAD, thio-NADP, and a compound according to formula (I) or a salt or optionally a reduced form thereof. However, inclusion of additional enzymes within the first reagent material is also contemplated.

The first reagent material may also include a mediator. The mediator can be selected as any chemical species (generally electroactive) which can participate in a reaction scheme involving the enzyme, the first analyte, and the coenzyme, and reaction products thereof, to produce a detectable electroactive reaction product. Typically, participation of the mediator in the reaction involves a change in its oxidation state (e.g., a reduction), upon interaction with any one of the first analyte, the enzyme, or the coenzyme, or a species that is a reaction product of one of these (e.g., a coenzyme reacted to a different oxidation state). A variety of mediators exhibit suitable electrochemical behavior. A mediator can preferably also be stable in its oxidized form, may optionally exhibit reversible redox electrochemistry, can preferably exhibit good solubility in aqueous solutions, and preferably reacts rapidly to produce an electroactive reaction product. Examples of mediators include benzoquinone, meldola blue, transition metal complexes such as potassium ferricyanide and osmium derivatives (see International Patent Publication No. WO 98/35225), and a combination of a phenazine derivative and hexaammineruthenium chloride (see U.S. Pat. No. 8,008,037). The first reagent material may also include a nitrosoaniline-based compound that acts as a mediator precursor (see e.g. U.S. Pat. No. 5,286,362). In this regard, the nitrosoaniline-based mediator precursor breaks down into reversible mediator components when it contacts an analyte sample such as blood.

Additional examples of mediators and nitrosoaniline-based mediator precursors include N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3,4-tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2- hydroxyethoxy)-2-hydroxy-1-propyl)-4-nitrosoaniline, and N-(2-hydroxyethyl)-N-(2-(2-hydroxyethoxy)-ethyl)-4-nitrosoaniline.

Reagent materials 62, 122 include a second coenzyme-dependent enzyme or a substrate for the second enzyme and a suitable coenzyme. These components are typically dissolved or suspended in a matrix. The liquid test sample hydrates or dissolves the matrix, and the analyte diffuses through the matrix to react with one or more of the active components. Suitable enzymes that could be included in reagent materials 62, 122 are for example dehydrogenases selected from glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1,1,6), alcohol dehydrogenase (E.C.1.1.1.1), hydroxybutyrate dehydrogenase (HBDH), such as 3-hydroxybutyrate dehydrogenase or beta-hydroxybutyrate dehydrogenase, alpha-hydroxybutyrate dehydrogenase and gamma-hydroxybutyrate dehydrogenase, sorbitol dehydrogenase, and amino acid dehydrogenase e.g. L-amino acid dehydrogenase (E.C.1.4.1.5). Further suitable enzymes are oxidases such as glucose oxidase (E.C.1.1.3.4) or cholesterol oxidase (E.C.1.1.3.6) or aminotransferases such as aspartate or alanine aminotransferase, 5'-nucleotidase or creatine kinase. Depending on the selected enzyme, potential coenzymes suitable for use in reagent materials 62, 122 include FAD, NAD, NADP, thio-NAD, thio-NADP, and a compound according to formula (I) or a salt or optionally a reduced form thereof.

In one embodiment where reagent materials 60, 120 are operable to facilitate detection of the presence and/or concentration of hydroxybutyrate, reagent materials 62, 122 are operable to facilitate detection of the presence and/or concentration of glucose and include an enzyme for glucose. In one particular form, the enzyme is a glucose dehydrogenase or a glucose oxidase. In this embodiment, reagent materials 62, 122 further include a coenzyme selected from FAD, NAD, NADP and the compound according to formula (I) or a salt or optionally a reduced form thereof. While not previously discussed, forms in which reagent materials 60 and 62 have a common coenzyme, e.g., a compound according to formula (I) or a salt or optionally a reduced form thereof, and are merged together to form a single reagent layer such that space 64 therebetween is eliminated are contemplated. It should also be understood that the reagent materials described herein for detecting the presence and/or concentration of glucose are not limiting, and that other forms for the same are known in the art. Additional non-limiting examples of reagent materials operable for detecting the presence and/or concentration of glucose are disclosed in U.S. Pat. No. 7,727,467 (incorporated herein above) and U.S. Pat. No. 8,008,037, the contents of which are incorporated herein by reference in their entirety. The second reagent material may also include a mediator. The mediator can be selected as any chemical species (generally electroactive) which can participate in a reaction scheme involving the second enzyme, the second analyte, and the coenzyme, and reaction products thereof, to produce a detectable electroactive reaction product. Typically, participation of the mediator in the reaction involves a change in its oxidation state (e.g., a reduction), upon interaction with any one of the second analyte, the second enzyme, or the coenzyme, or a species that is a reaction product of one of these (e.g., a coenzyme reacted to a different oxidation state). A variety of mediators exhibit suitable electrochemical behavior. A mediator can preferably also be stable in its oxidized form, may optionally exhibit reversible redox electrochemistry, can preferably exhibit good solubility in aqueous solutions, and preferably reacts rapidly to produce an electroactive reaction product. Examples of mediators include benzoquinone, meldola blue, transition metal complexes such as potassium ferricyanide and osmium derivatives (see International Patent Publication No. WO 98/35225), and a combination of a phenazine derivative and hexaammineruthenium chloride (see U.S. Pat. No. 8,008,037). The second reagent material may also include a nitrosoaniline-based compound that acts as a mediator precursor (see e.g. U.S. Pat. No. 5,286,362). In this regard, the nitrosoaniline-based mediator precursor breaks down into reversible mediator components when it contacts an analyte sample such as blood.

Additional examples of mediators and nitrosoaniline-based mediator precursors include N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3,4-tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, and N-(2-hydroxyethyl)-N-(2-(2-hydroxyethoxy)-ethyl)-4-nitrosoaniline.

The reagent materials may also include a variety of adjuvants to enhance various properties or characteristics thereof. See e.g., U.S. Pat. No. 7,749,437 referred to hereinabove. For example, reagent materials 60, 62 and 120, 122 may include materials to facilitate their placement onto respective substrates 16, 114 and to improve their adherence thereto, or for increasing the rate of hydration of the reagent materials by the sample fluid. Additionally, the reagent materials can include components selected to enhance the physical properties of the resulting dried reagent layer, and the uptake of a liquid test sample for analysis. Examples of adjuvant materials to be used with the reagent materials include thickeners, viscosity modulators, film formers, stabilizers, buffers, detergents, gelling agents, fillers, film openers, coloring agents, and agents endowing thixotropy.

Non-limiting examples of thickeners that may be included in the reagent materials include (1) starches, gums (e.g., pectin, guar gum, locust bean (carob seed) gum, konjac gum, xanthan gum, alginates, and agar), casein, gelatin, and phycocolloids; (2) cellulose and semi-synthetic cellulose derivatives (carboxymethyl-cellulose, methyl cellulose, hydroxymethylcellulose, hydroxyethylcellulose, methylhydroxyethylcellulose); (3) polyvinyl alcohol and carboxy-vinylates; and (4) bentonite, silicates, and colloidal silica. More specific forms of thickeners include a combination of a xanthan gum sold under the trade name Keltrol F by CP Kelco US, Inc., and carboxylmethyl cellulose sold under the trade name AQUALON® CMC 7F PH by Hercules Inc., Aqualon Division.

Film forming and thixotropic agents that can be included in the reagent materials include polymers and silica. One more specific thixotropic agent includes silica sold under the trade name Kieselsaure Sipemate FK 320 DS by Degussa AG, while a more specific film forming agent includes polyvinylpyrrolidone, sold under the trademark polyvinylpyrrolidone Kollidon 25, by BASF, and polyvinyl propionate dispersion.

Stabilizers for the enzymes in the reagent materials can be selected from saccharides and mono- or di-fatty acid salts. More specific stabilizers include trehalose sold under the trade name D-(+)-Trehalose dihydrate by Sigma Chemical Co. and sodium succinate.

Non-limiting examples of detergents that can be included in the reagent materials include water-soluble soaps, as well as water-soluble synthetic surface-active compounds such as alkali, earth alkali or optionally substituted ammonium salts of higher fatty acids, e.g., oleic or stearic acid, mixtures of natural fatty acids, for example, from coconut or tallow oil, fatty sulphates, esters of sulphonic acids, salts of alkyl sulphonic acids taurine salts of fatty acids, fatty acid amides, and ester amides. More specific forms of detergents include an ester amide, n-octanoyl-N-methylglucamide, sold under the trade name Mega-8 by Dojindo Molecular Technologies, Inc., and a fatty acid salt, N-methyl oleyl taurate sodium salt, sold under the trade name Geropon T77 by Rhodia HPCII (Home, Personal Care and Industrial Ingredients).

In one form, the reagent materials are formulated as a viscous solution that includes thickeners and thixotropic agents to enhance its physical properties. The thickeners are selected to provide a thick, liquid matrix having the remaining components homogeneously dispersed therein. The thickening and thixotropic agents also inhibit the liquid or semi-paste material from running or spreading over the surface of substrates 16, 114 after it has been deposited and before it dries. After the reagent materials are deposited, they quickly dry to a readily hydratable matrix.

As indicated above, it has been surprisingly discovered that detection of the presence and/or concentration of hydroxybutyrate can be completed in or about five seconds after the test element has been contacted with the sample in forms where the first reagent material includes a hydroxybutyrate dehydrogenase and a coenzyme selected from thio-NAD, thio-NADP, and a compound according to formula (I) or a salt or optionally a reduced form thereof. Current state of the art for glucose testing facilitates the detection of the presence and/or concentration of glucose to be completed in or about five seconds after the test element has been contacted with the sample. U.S. Pat. No. 8,008,037 describes one non-limiting form of glucose testing that facilitates detection of the presence and/or concentration of glucose within this timeframe. Additional, non-limiting forms of glucose testing that facilitates detection of the presence and/or concentration of glucose within this timeframe are described in U.S. Pat. Nos. 7,276,146 and 7,276,147, the contents of both being hereby incorporated herein by reference in their entirety. It should be understood however that other reagent materials which facilitate detection of the presence and/or concentration of glucose within this or other timeframes are known and could be used in the test elements disclosed herein.

In view of the foregoing, it should be appreciated that detection of the presence and/or concentration of hydroxybutyrate and glucose can be completed within five seconds after the test element has been contacted by the sample when the test element includes a first reagent material that has a hydroxybutyrate dehydrogenase and a coenzyme selected from thio-NAD, thio-NADP, and a compound according to formula (I) or a salt or optionally a reduced form thereof, and a second reagent material that is suitable for detection of glucose and appropriately formulated. However, it should also be understood that variations in the timing for completing the detection of hydroxybutyrate and glucose with these test elements is also possible and dependent on, for example, the specific formulation of the reagent materials, amongst other aspects. In one form for example, the detection of hydroxybutyrate and glucose is completed within 10 seconds after the test element has been contacted by the sample. In another form, the detection of hydroxybutyrate and glucose is completed within 7.5 seconds after the test element has been contacted by the sample. It should also be appreciated that the timing for completion of the hydroxybutyrate detection and the glucose detection may be different. For example, in one or more of the foregoing or other forms the hydroxybutyrate detection is completed within 4 seconds before or after completion of the glucose detection. In another variant, the hydroxybutyrate detection is completed within 2 seconds before or after completion of the glucose detection. In still another variant, the hydroxybutyrate detection is completed at or near the same time the glucose detection is completed. It should be understood however that other variations in the timeframe for completion of hydroxybutyrate and glucose detection are contemplated.

EXAMPLES

The following examples are for illustration purposes and are not to be construed as limiting the invention disclosed in this document to only the embodiments disclosed in these examples.

Reagent Material Formulation

Figure 6:
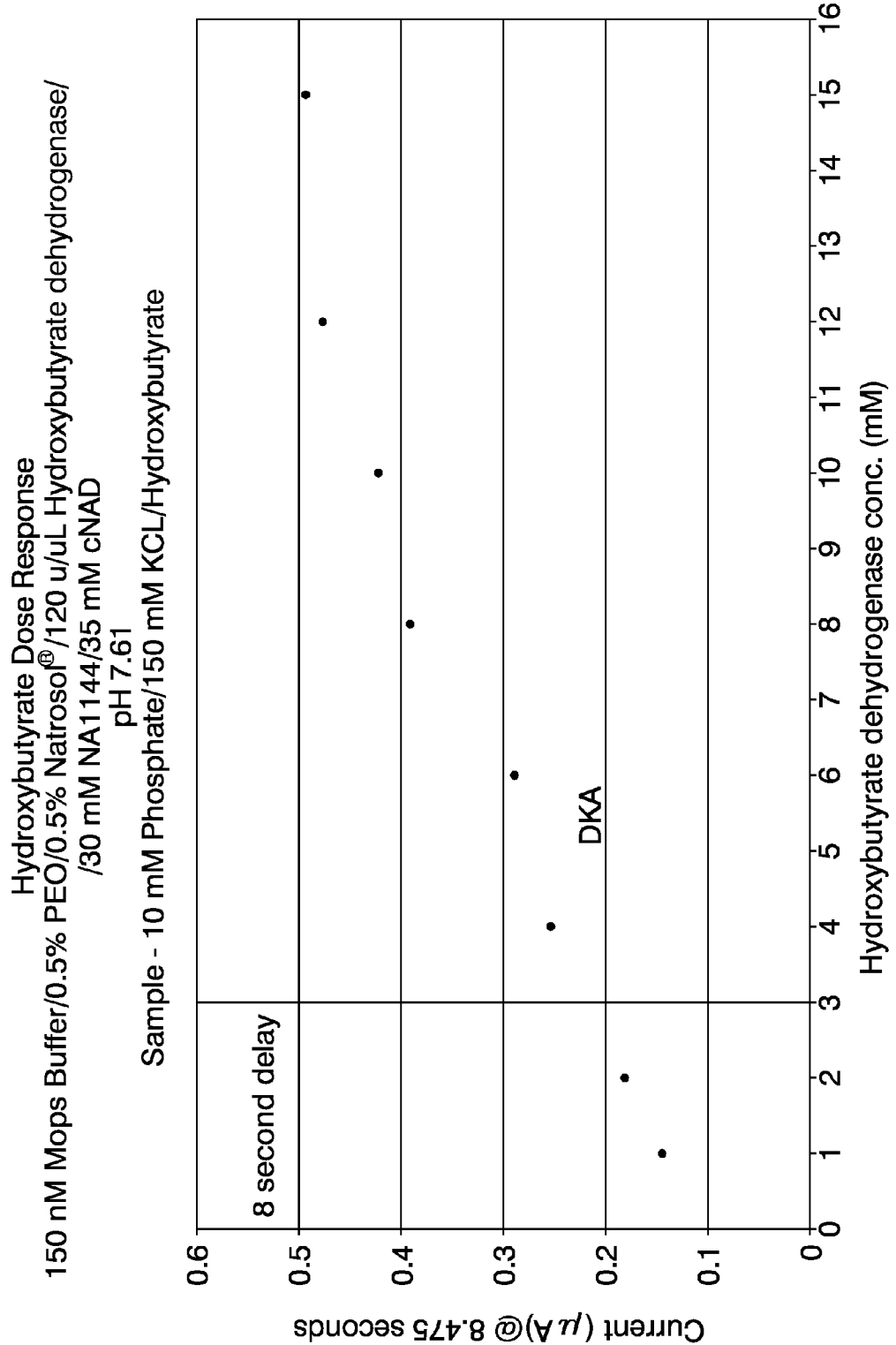
FIGS. 6-18 are graphical illustrations of hydroxybutyrate responses determined with various reagent materials.

Reagent Material of FIG. 6

A stock buffer solution was prepared by adding 7.344 g of MOPS sodium salt, 0.125 g of Triton™ X-100 (a nonionic detergent from Sigma-Aldrich Corporation, St. Louis, Mo.), 2.400 g of trehalose, and 2.026 g of sodium sucinnate hexahydrate to 400 mL of double distilled water and adjusting the solution's pH to 8.14. This solution was added to a 500 mL volumetric flask and diluted with double distilled water to make a 500 mL solution.

Preparation of a buffer/Natrosol/PEO polymer solution was completed by combining 396 g of the initial buffer solution with 2 g of polyethylene oxide (300K) and 2 g of Natrosol® 250 M (a nonionic, water-soluble hydroxyethylcellulose polymer from Ashland, Inc., Covingtion, Ky.). The mixture was mixed overnight before use.

A nitrosoaniline/carba-NAD reagent material was prepared by adding the following ingredients to a 20 mL speed mixing cup containing 5.0595 g of buffer/polymer stock solution in a serial fashion: a) 0.0415 g of a substituted nitrosoaniline derivative (NA 1144 provided by Roche Diagnostics, Inc.) was added to the container and the matrix was mixed for 1 minute at 24,000 rpm and the pH was adjusted to 7.7; b) 0.0692 g of carba-NAD free acid was added to a 10 mL speed mixing cup containing 3 mL of the nitrosoaniline solution, and the matrix was mixed for 1 minute at 24,000 rpm and the pH was adjusted to 7.2; and c) 0.2134 g of beta-hydroxybutyrate dehydrogenase from *alcaligenes faecalis* was added to the cup and speed mixed for 2 minutes at 24,000 rpm.

Figure 7:
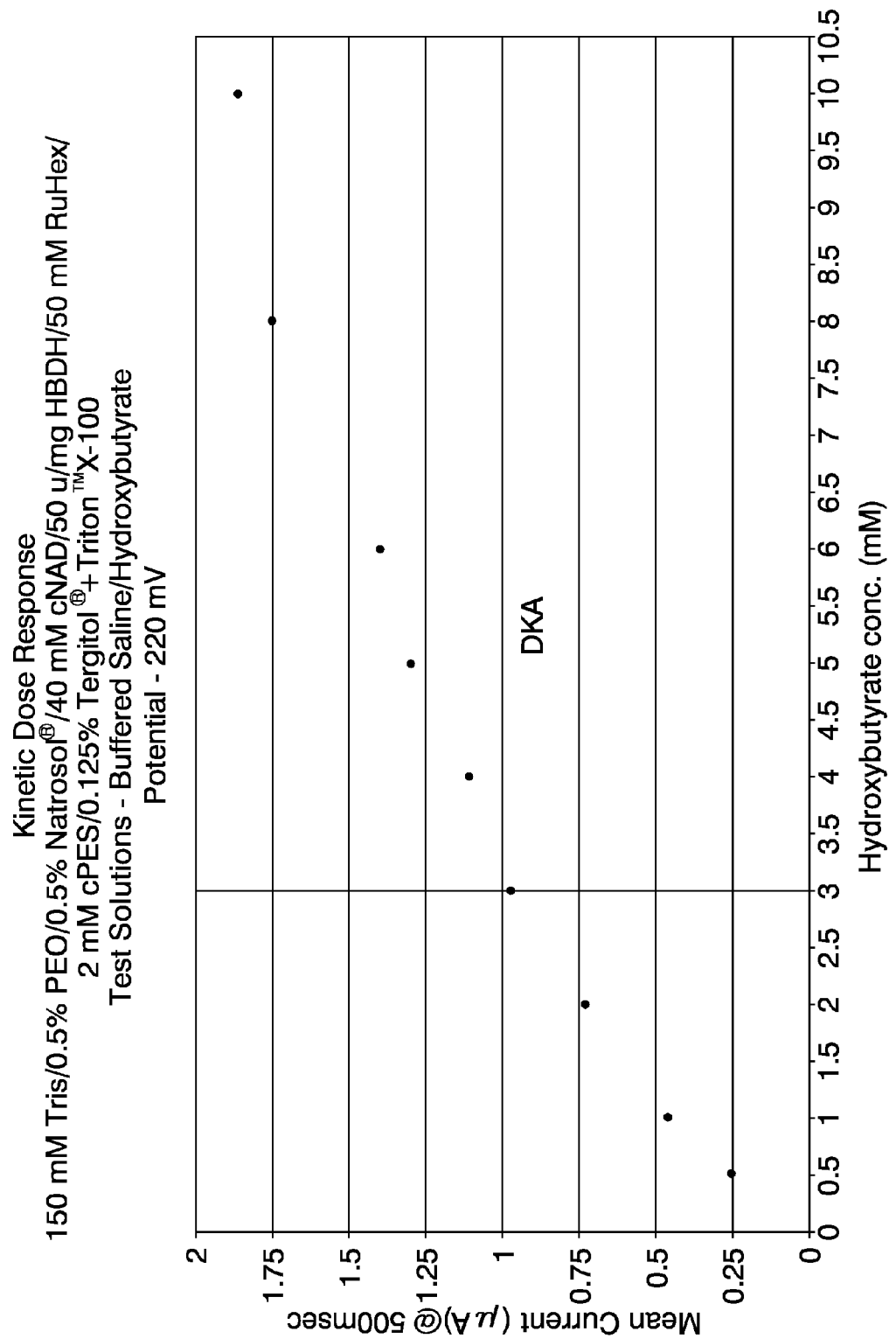

Reagent Material of FIG. 7

A stock buffer solution was prepared by adding 9.086 g of Tris base, 0.125 g of Triton™ X-100, 0.625 g of Tergitol® 15-S-9 (a nonionic surfactant from The Dow Chemical Company, Midland, Mich.), 2.400 g of trehalose, and 2.026 g of sodium sucinnate hexahydrate to 400 mL of double distilled water and adjusting the solution's pH to 7.95. This solution was added to a 500 mL volumetric flask and diluted with double distilled water to make a 500 mL solution.

Preparation of a buffer/Natrosol®/PEO polymer solution was completed by combining 396 g of the initial buffer solution with 2 g of polyethylene oxide (300K) and 2 g of Natrosol® 250 M. The mixture was mixed overnight before use. A hexaammineruthenium/carba-NAD reagent material was prepared by adding the following ingredients to a 20 mL speed mixing cup containing 4.048 g of buffer/polymer stock solution in a serial fashion: a) 0.0619 g of hexaammineruthenium chloride and b) 0.0034 g of 1-(3-carbroxypropyloxy)-5-ethyl phenazine were added to the cup and the matrix was mixed for 1 minute at 24,000 rpm and the pH was adjusted to 7.9; and c) 0.0791 g of carba-NAD free acid was added to a 10 mL speed mixing cup containing 3 mL of the hexaammineruthenium/phenazine solution, and the matrix was mixed for 1 minute at 24,000 rpm and the pH was adjusted to 7.24. 0.0862 g of beta-hydroxybutyrate dehydrogenase from *alcaligenes faecalis* was then added to the cup and speed mixed for 2 minutes at 24,000 rpm.

Figure 8:
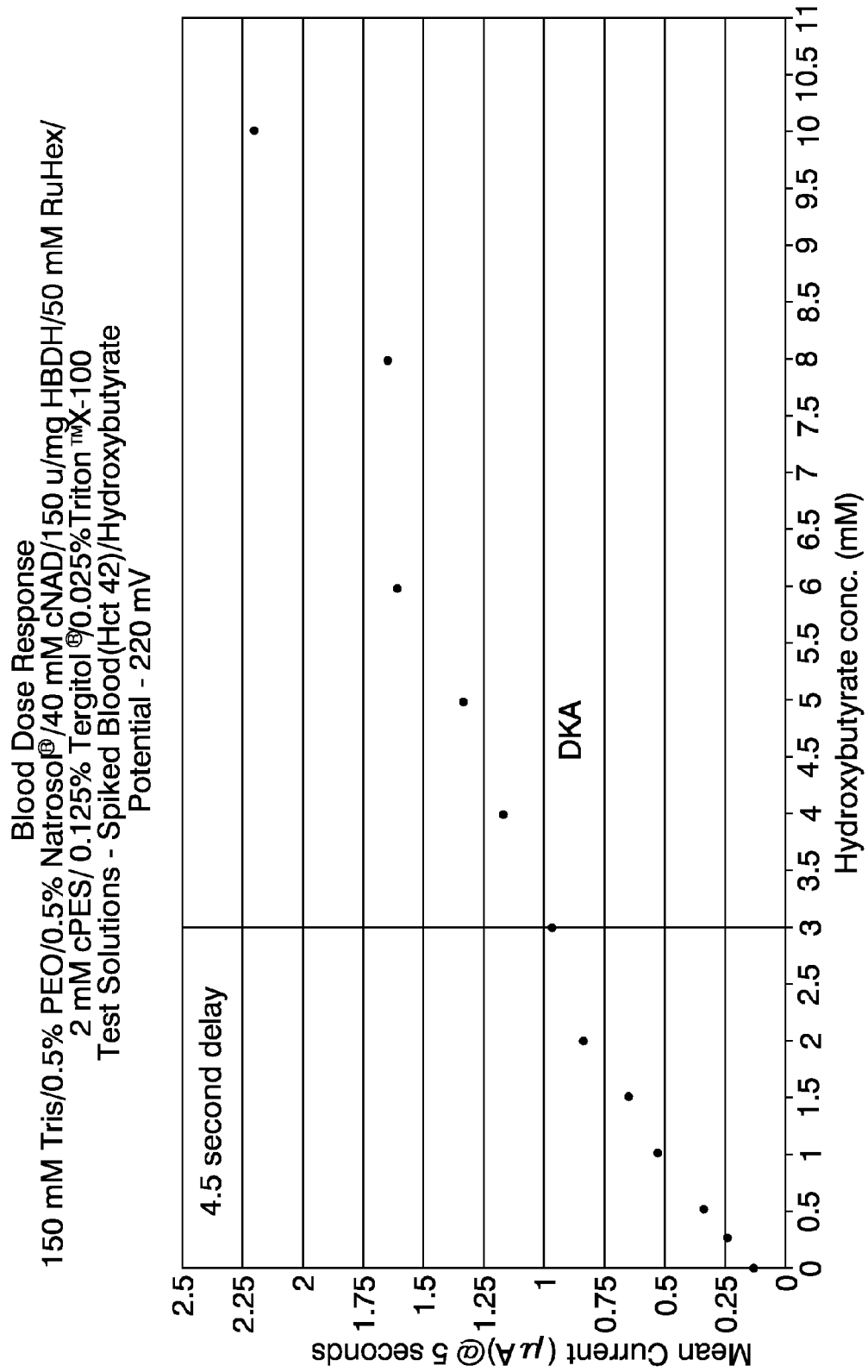
Figure 9:
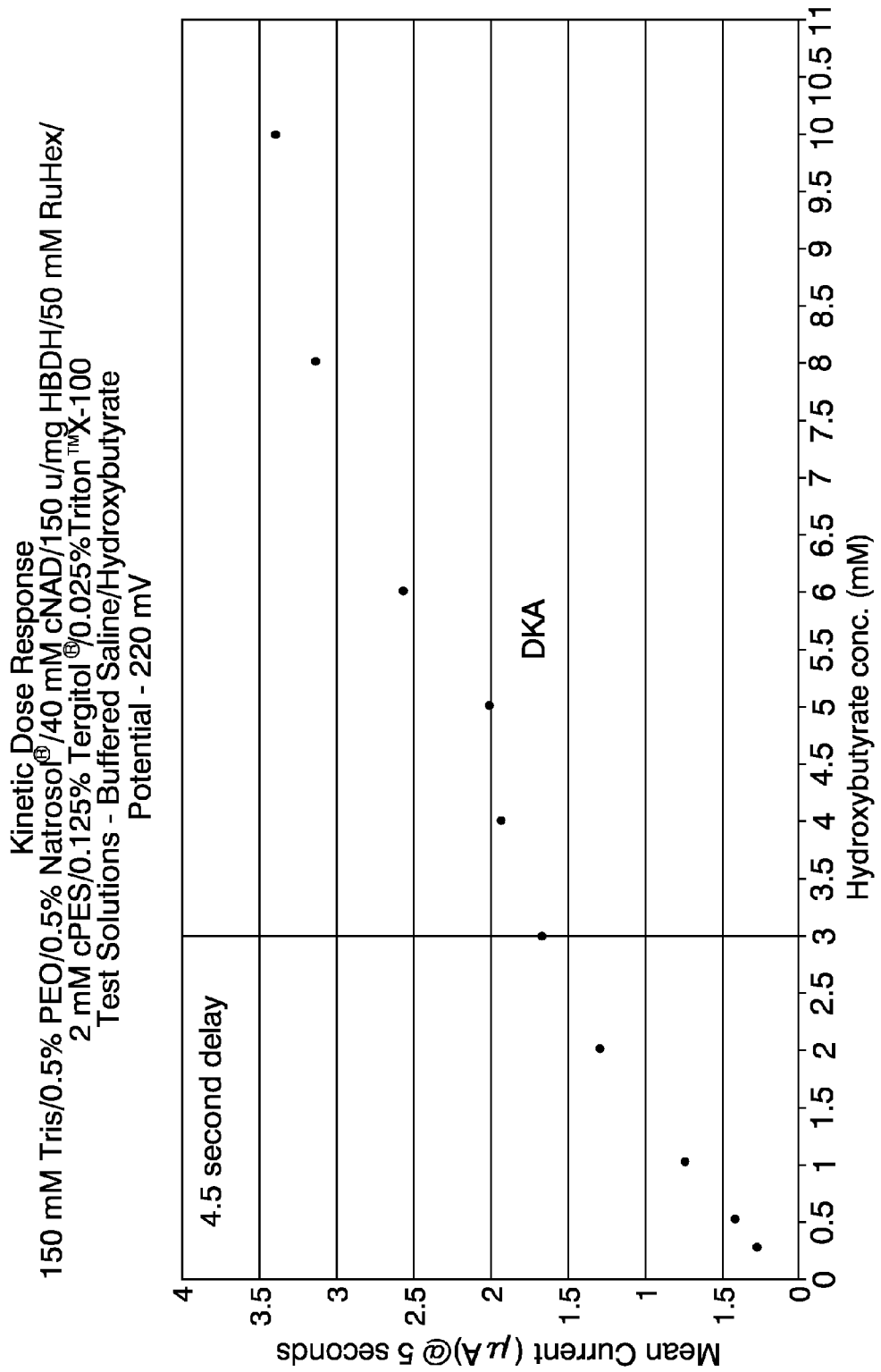

Reagent Material of FIGS. 8 and 9

A hexaammineruthenium/carba-NAD reagent material was prepared by adding the following ingredients to a 20 mL speed mixing cup containing 4.048 g of the Tris buffer/PEO/Natrosol® polymer stock solution described above in connection with the reagent material of FIG. 7 in a serial fashion: a) 0.062 g of hexaammineruthenium chloride and b) 0.003 g of 1-(3-carbroxypropyloxy)-5-ethyl phenazine were added to the cup and the matrix was mixed for 1 minute at 24,000 rpm and the pH was adjusted to 7.9; and c) 0.079 g of carba-NAD free acid was added to a 10 mL speed mixing cup containing 3 mL of the hexaammineruthenium/phenazine solution, and the matrix was mixed for 1 minute at 24,000 rpm and the pH was adjusted to 7.24. 0.259 g of beta-hydroxybutyrate dehydrogenase from *alcaligenes faecalis* was then added to the container and speed mixed for 2 minutes at 24,000 rpm.

Figure 10:
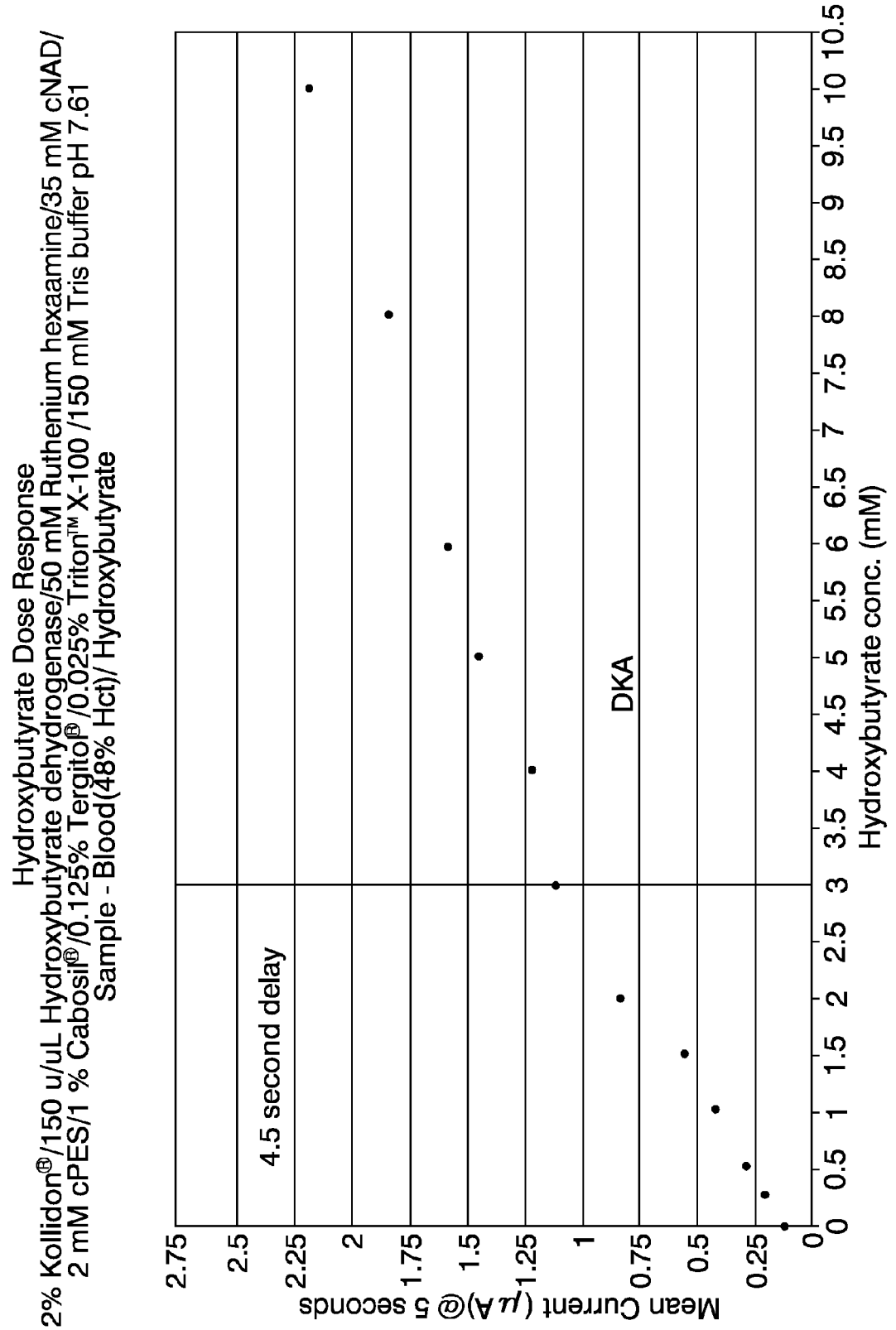

Reagent Material of FIG. 10

A stock buffer solution was prepared by adding 9.086 g of Tris base, 0.125 g of Triton™ X-100, 0.625 g of Tergitol® 15-S-9, 2.40 g of trehalose, and 2.026 g of sodium sucinnate hexahydrate to 400 mL of double distilled water and adjusting the solution's pH to 7.95. This solution was added to a 500 mL volumetric flask and diluted with double distilled water to make a 500 mL solution.

Preparation of a buffer/Kollidon® VA 64 polymer solution was completed by combining 392 g of the initial buffer solution with 8 g of Kollidon® VA 64 (a vinylpyrrolidone-vinyl acetate copolymer from BASF Corporation, Florham Park, N.J.). The mixture was mixed overnight before use.

A nitrosoaniline/carba-NAD reagent material was prepared by adding the following ingredients to a 20 mL speed mixing cup containing 6.071 g of buffer/polymer stock solution in a serial fashion: a) 0.0600 g of untreated fumed silica (Cabosil®, Cabot Corporation, Boston, Mass.) and b) 0.050 g of a substituted nitrosoaniline derivative (NA 1144 provided by Roche Diagnostics, Inc., Indianapolis, Ind.) were added to the cup and the matrix was mixed for 1 minute at 24,000 rpm and the pH was adjusted to 7.9; c) 0.069 g of carba-NAD free acid was added to a 10 mL speed mixing cup containing 3 mL of the nitrosoaniline solution, and the matrix was mixed for 1 minute at 24,000 rpm and the pH was adjusted to 7.2; and d) 0.259 g of beta-hydroxybutyrate dehydrogenase from *alcaligenes faecalis* was added to the cup and speed mixed for 2 minutes at 24,000 rpm.

Figure 11:
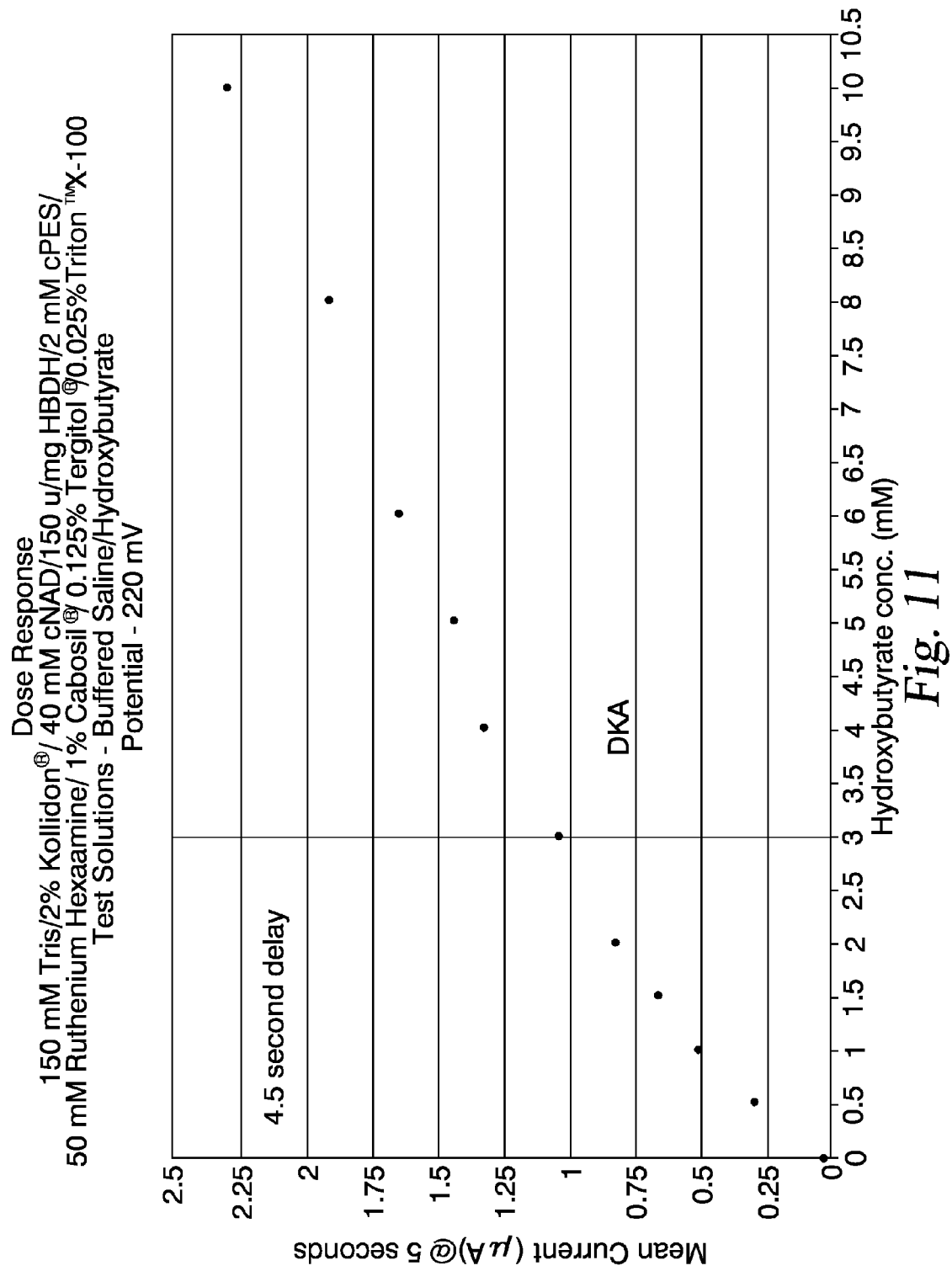

Reagent Material of FIG. 11

A hexaammineruthenium/carba-NAD reagent material was prepared by adding the following ingredients to a 20 mL speed mixing cup containing 4.049 g of the Tris/Kollidon® buffer polymer stock solution described above in connection with the reagent material of FIG. 10 in a serial fashion: a) 0.040 g of untreated fumed silica (Cabosil®, Cabot Corporation, Boston, Mass.), b) 0.062 g of hexaammineruthenium chloride, and c) 0.003 g of 1-(3-carbroxypropyloxy)-5-ethyl phenazine were added to the cup and the matrix was mixed for 1 minute at 24,000 rpm and the pH was adjusted to 7.9; d) 0.079 g of carba-NAD free acid was added to a 10 mL speed mixing cup containing 3 mL of the hexaammineruthenium/phenazine solution, and the matrix was mixed for 1 minute at 24,000 rpm and the pH was adjusted to 7.2; and e) 0.259 g of beta-hydroxybutyrate dehydrogenase from *alcaligenes faecalis* was added to the cup and speed mixed for 2 minutes at 24,000 rpm.

Figure 12:
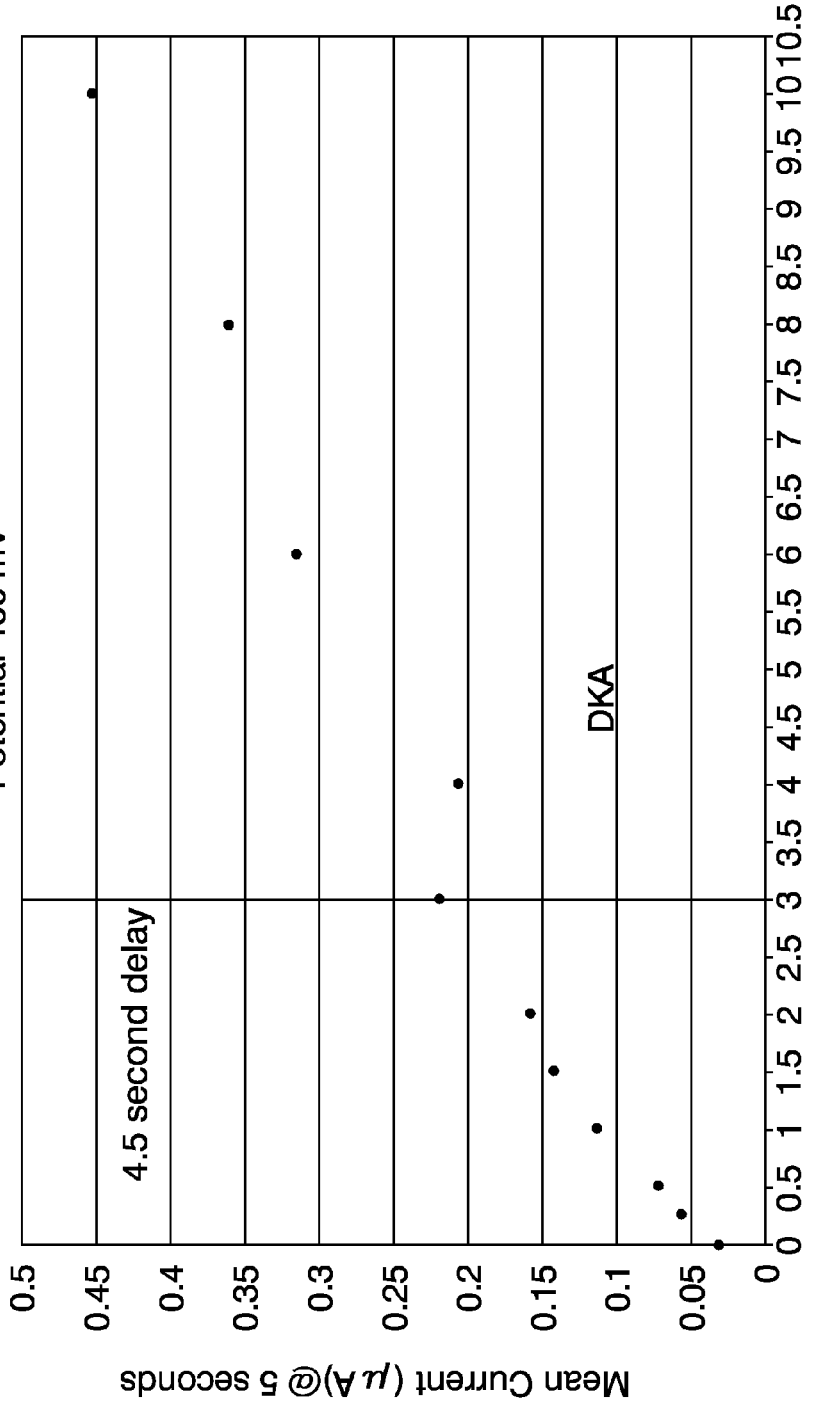

Reagent Material of FIG. 12

A nitrosoaniline/carba-NAD reagent material was prepared by adding the following ingredients to a 20 mL speed mixing cup containing 6.074 g of the Tris/Kollidon® buffer/polymer stock solution described above in connection with the reagent material of FIG. 10 in a serial fashion: a) 0.060 g of untreated fumed silica (Cabosil®, Cabot Corporation, Boston, Mass.) and b) 0.050 g of a substituted nitrosoaniline derivative (NA 1144 provided by Roche Diagnostics, Inc., Indianapolis, Ind.) were added to the cup and the matrix was mixed for 1 minute at 24,000 rpm and the pH was adjusted to 7.8; c) 0.069 g of carba-NAD free acid was added to a 10 mL speed mixing cup containing 3 mL of the nitrosoaniline solution, and the matrix was mixed for 1 minute at 24,000 rpm and the pH was adjusted to 7.2; and e) 0.259 g of beta-hydroxybutyrate dehydrogenase from *alcaligenes faecalis* was added to the cup and speed mixed for 2 minutes at 24,000 rpm.

Figure 13:
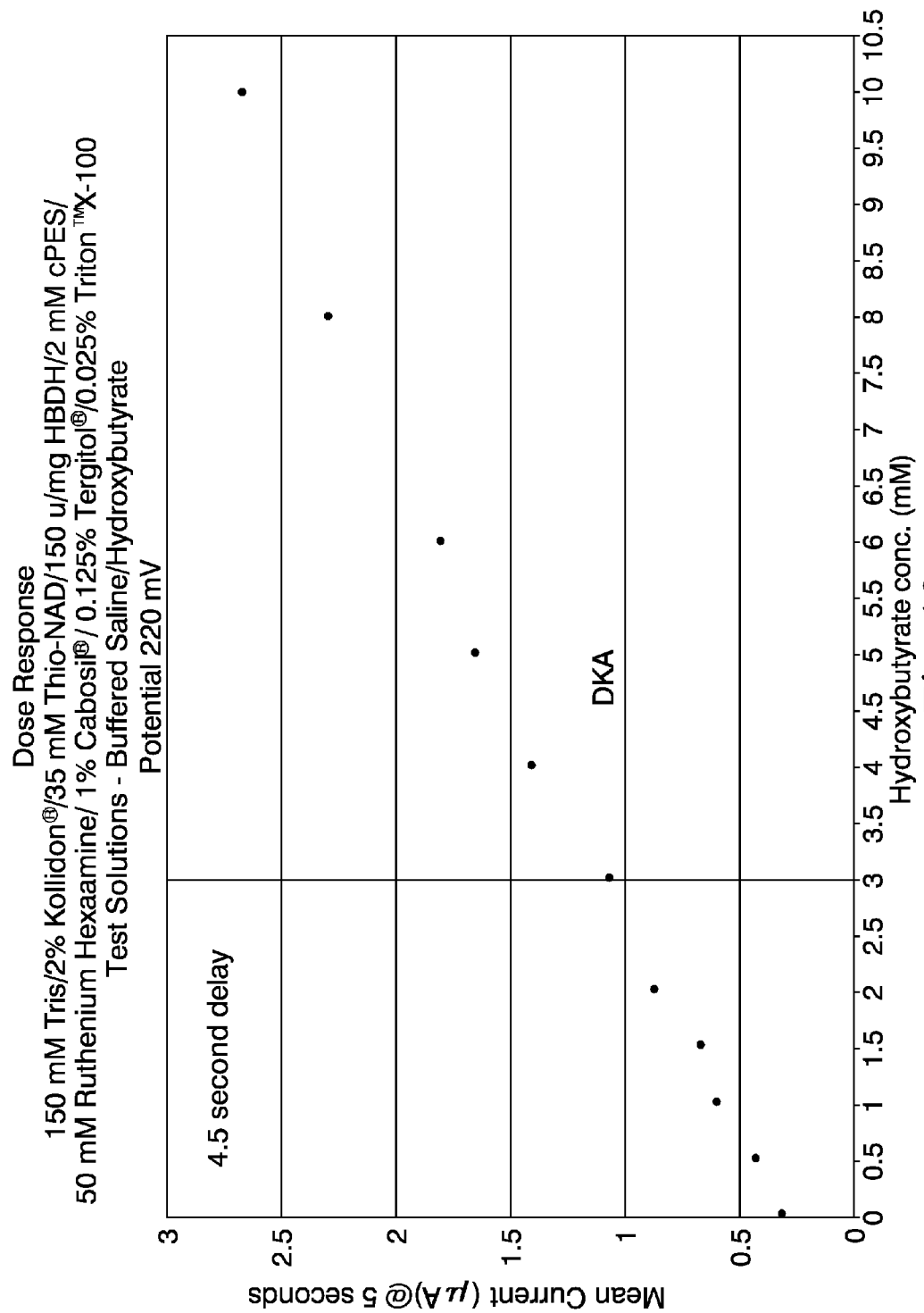

Reagent Material of FIG. 13

A hexaammineruthenium/Thio-NAD reagent material was prepared by adding the following ingredients to a 20 mL speed mixing cup containing 6.074 g of the Tris/Kollidon® buffer polymer stock solution described above in connection with the reagent material of FIG. 10 in a serial fashion: a) 0.060 g of untreated fumed silica (Cabosil®, Cabot Corporation, Boston, Mass.), b) 0.093 g of hexaammineruthenium chloride and c) 0.005 g of 1-(3-carbroxypropyloxy)-5-ethyl phenazine were added to the cup and the matrix was mixed for 1 minute at 24,000 rpm and the pH was adjusted to 7.9; d) 0.079 g of Thio-NAD free acid was added to a 10 mL speed mixing cup containing 3 mL of the hexaammineruthenium/phenazine solution, and the matrix was mixed for 1 minute at 24,000 rpm and the pH was adjusted to 7.2; and e) 0.259 g of beta-hydroxybutyrate dehydrogenase from *alcaligenes faecalis* was added to the cup and speed mixed for 2 minutes at 24,000 rpm.

Figure 14:
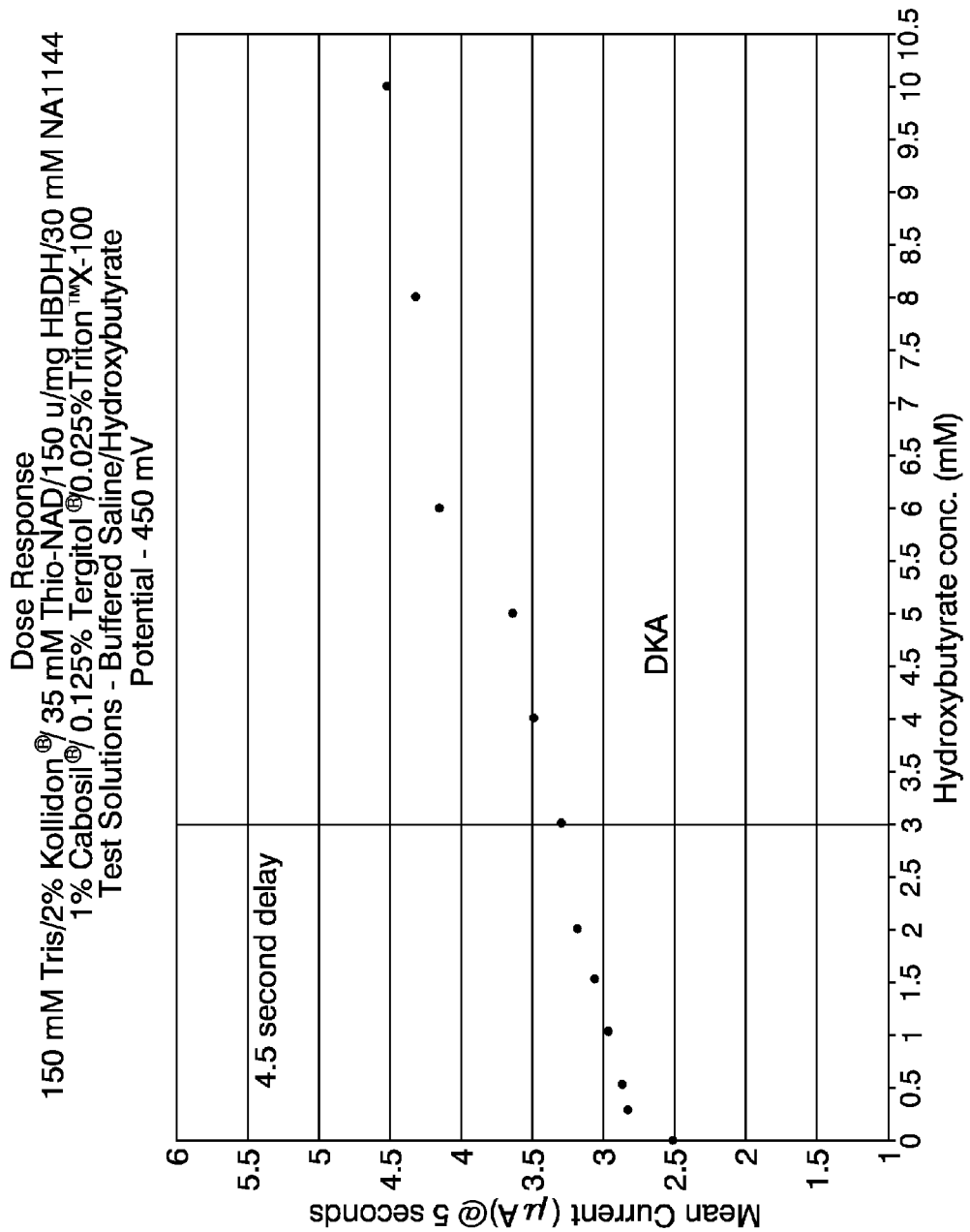

Reagent Material of FIG. 14

A nitrosoaniline/Thio-NAD reagent material was prepared by adding the following ingredients to a 20 mL speed mixing cup containing 6.074 g of the Tris/Kollidon® buffer/polymer stock solution described above in connection with the reagent material of FIG. 10 in a serial fashion: a) 0.060 g of untreated fumed silica (Cabosil®, Cabot Corporation, Boston, Mass.) and b) 0.050 g of a substituted nitrosoaniline derivative (NA 1144 provided by Roche Diagnostics, Inc., Indianapolis, Ind.) were added to the cup and the matrix was mixed for 1 minute at 24,000 rpm and the pH was adjusted to 7.8; c) 0.079 g of Thio-NAD free acid was added to a 10 mL speed mixing cup containing 3 mL of the nitrosoaniline solution, and the matrix was mixed for 1 minute at 24,000 rpm and the pH was adjusted to 7.2; and d) 0.259 g of beta-hydroxybutyrate dehydrogenase from *alcaligenes faecalis* was added to the cup and speed mixed for 2 minutes at 24,000 rpm.

Figure 15:
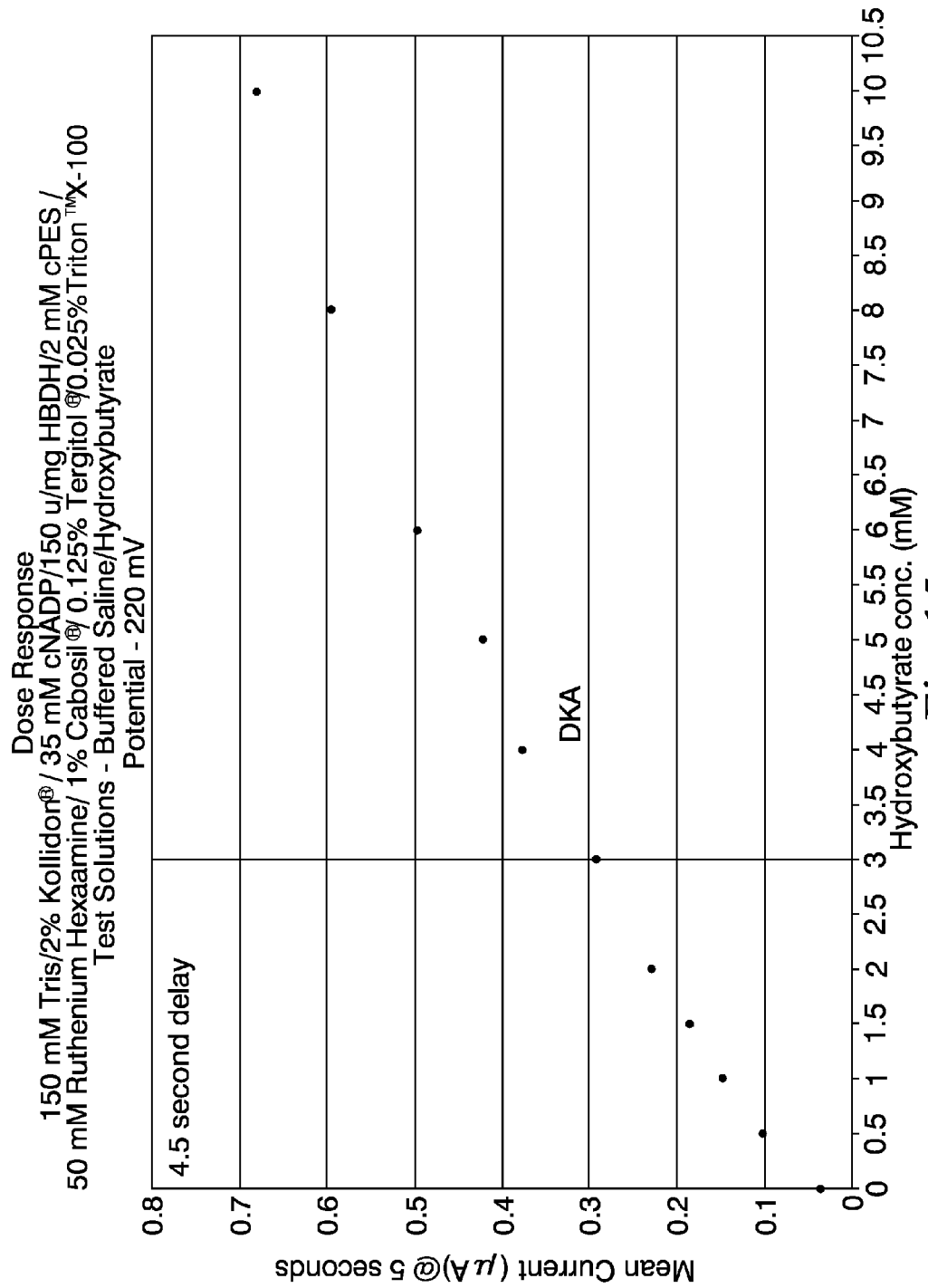

Reagent Material of FIG. 15

A hexaammineruthenium/carba-NADP reagent material was prepared by adding the following ingredients to a 20 mL speed mixing cup containing 6.074 g of the Tris/Kollidon® buffer polymer stock solution described above in connection with the reagent material of FIG. 10 in a serial fashion: a) 0.060 g of untreated fumed silica (Cabosil®, Cabot Corporation, Boston, Mass.), b) 0.093 g of hexaammineruthenium chloride and c) 0.005 g of 1-(3-carbroxypropyloxy)-5-ethyl phenazine were added to the cup and the matrix was mixed for 1 minute at 24,000 rpm and the pH was adjusted to 7.9; c) 0.076 g of carba-NADP free acid was added to a 10 mL speed mixing cup containing 3 mL of the hexaammineruthenium/phenazine solution, and the matrix was mixed for 1 minute at 24,000 rpm and the pH was adjusted to 7.2; and d) 0.259 g of beta-hydroxybutyrate dehydrogenase from *alcaligenes faecalis* was added to the cup and speed mixed for 2 minutes at 24,000 rpm.

Figure 16:
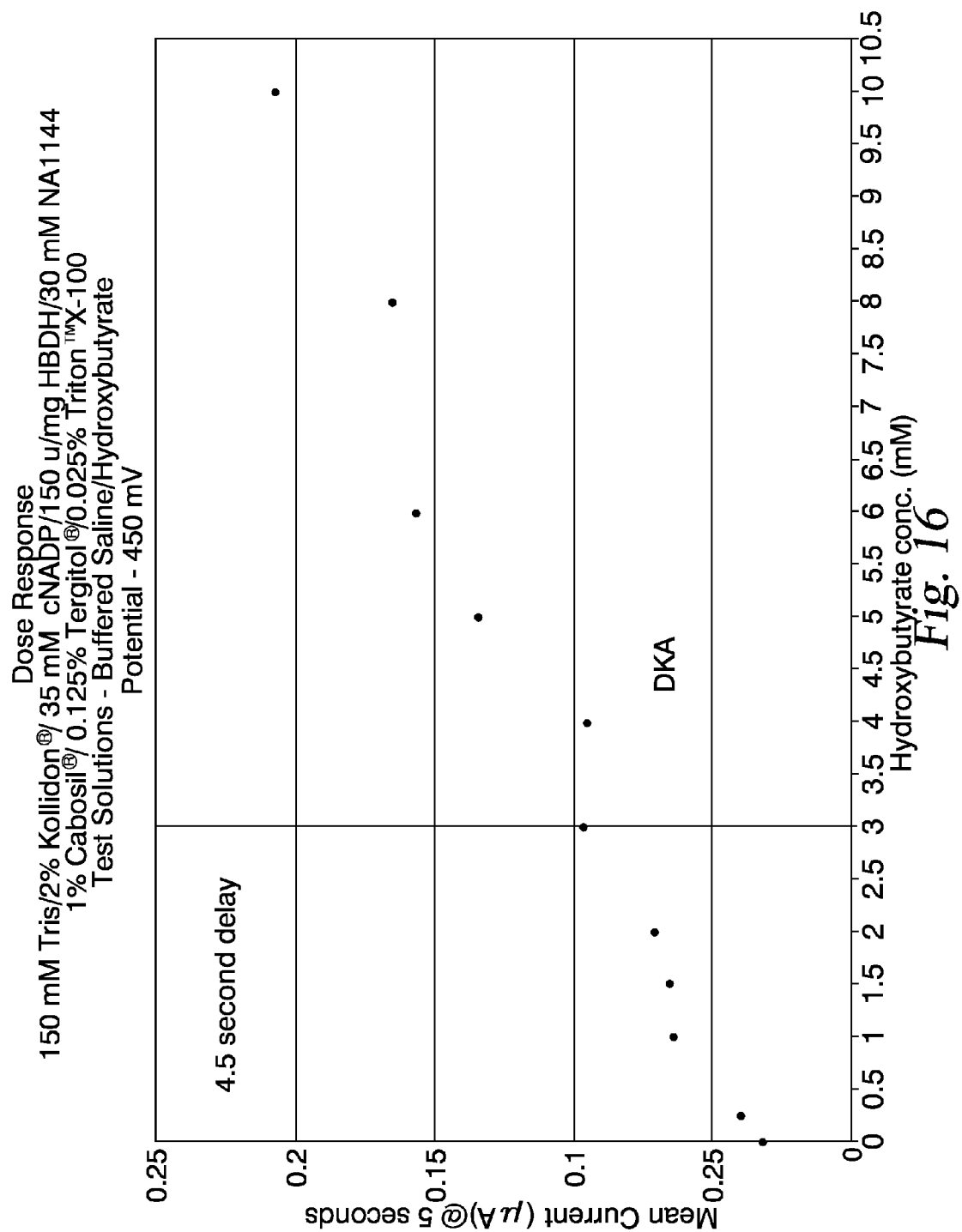

Reagent Material of FIG. 16

A nitrosoaniline/carba-NADP reagent material was prepared by adding the following ingredients to a 20 mL speed mixing cup containing 6.074 g of the Tris/Kollidon® buffer/polymer stock solution described above in connection with the reagent material of FIG. 10 in a serial fashion: a) 0.060 g of untreated fumed silica (Cabosil®, Cabot Corporation, Boston, Mass.) and b) 0.050 g of a substituted nitrosoaniline derivative (NA 1144 provided by Roche Diagnostics, Inc., Indianapolis, Ind.) were added to the cup and the matrix was mixed for 1 minute at 24,000 rpm and the pH was adjusted to 7.8; c) 0.076 g of carba-NADP free acid was added to a 10 mL speed mixing cup containing 3 mL of the nitrosoaniline solution, and the matrix was mixed for 1 minute at 24,000 rpm and the pH was adjusted to 7.2; and d) 0.259 g of beta-hydroxybutyrate dehydrogenase from *alcaligenes faecalis* was added to the cup and speed mixed for 2 minutes at 24,000 rpm.

Figure 17:
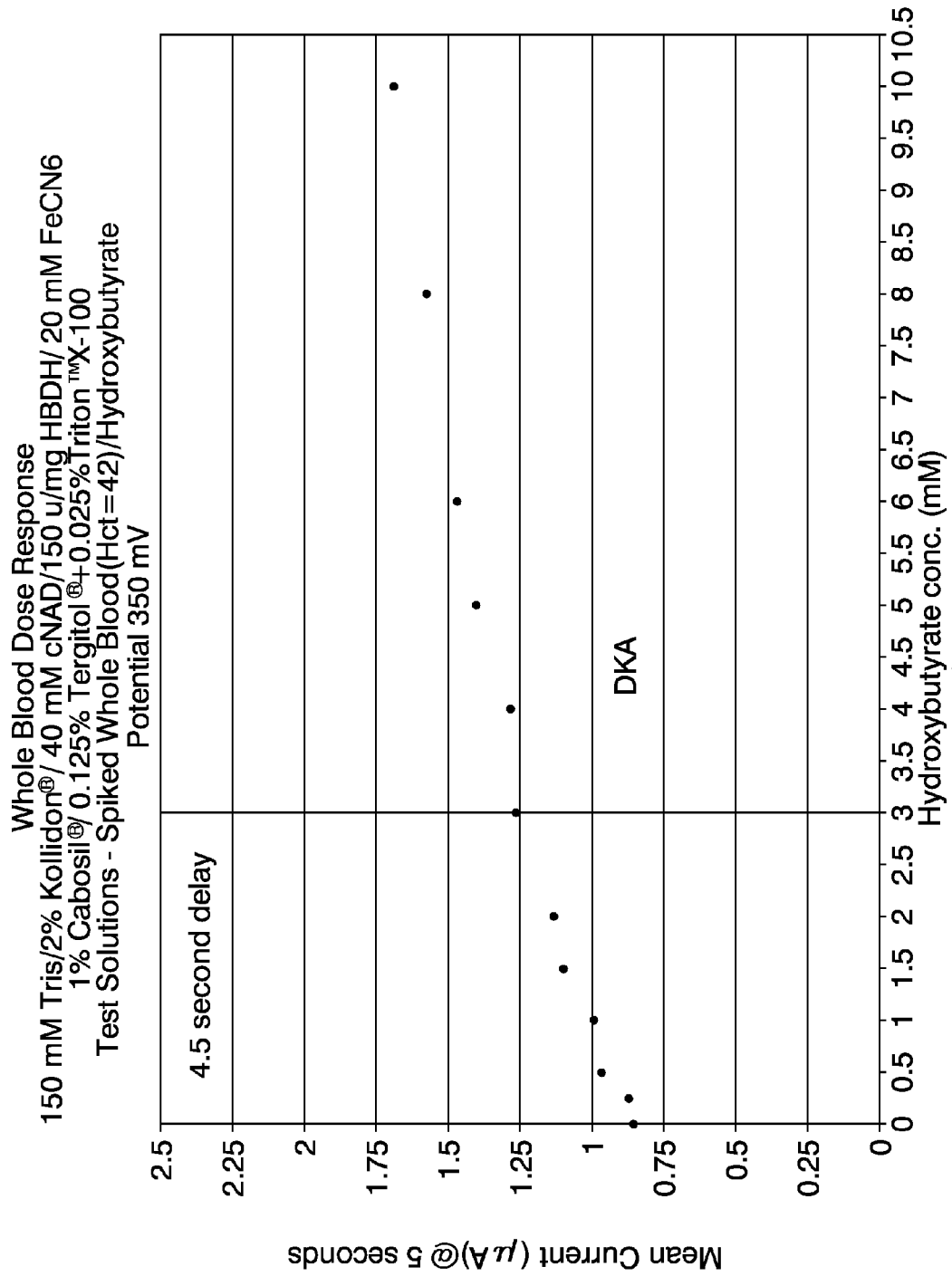

Reagent Material of FIG. 17

A ferricyanide/carba-NAD reagent material was prepared by adding the following ingredients to a 20 mL speed mixing cup containing 4.049 g of the Tris/Kollidon® buffer/polymer stock solution described above in connection with the reagent material of FIG. 10 in a serial fashion: a) 0.040 g of untreated fumed silica (Cabosil®, Cabot Corporation, Boston, Mass.) and b) 0.026 g of potassium ferricyanide were added to the cup and the matrix was mixed for 1 minute at 24,000 rpm and the pH was adjusted to 7.8; c) 0.076 g of carba-NAD free acid was added to a 10 mL speed mixing cup containing 3 mL of the ferricyanide solution, and the matrix was mixed for 1 minute at 24,000 rpm and the pH was adjusted to 7.2; and d) 0.259 g of beta-hydroxybutyrate dehydrogenase from *alcaligenes faecalis* was added to the cup and speed mixed for 2 minutes at 24,000 rpm.

Figure 18:
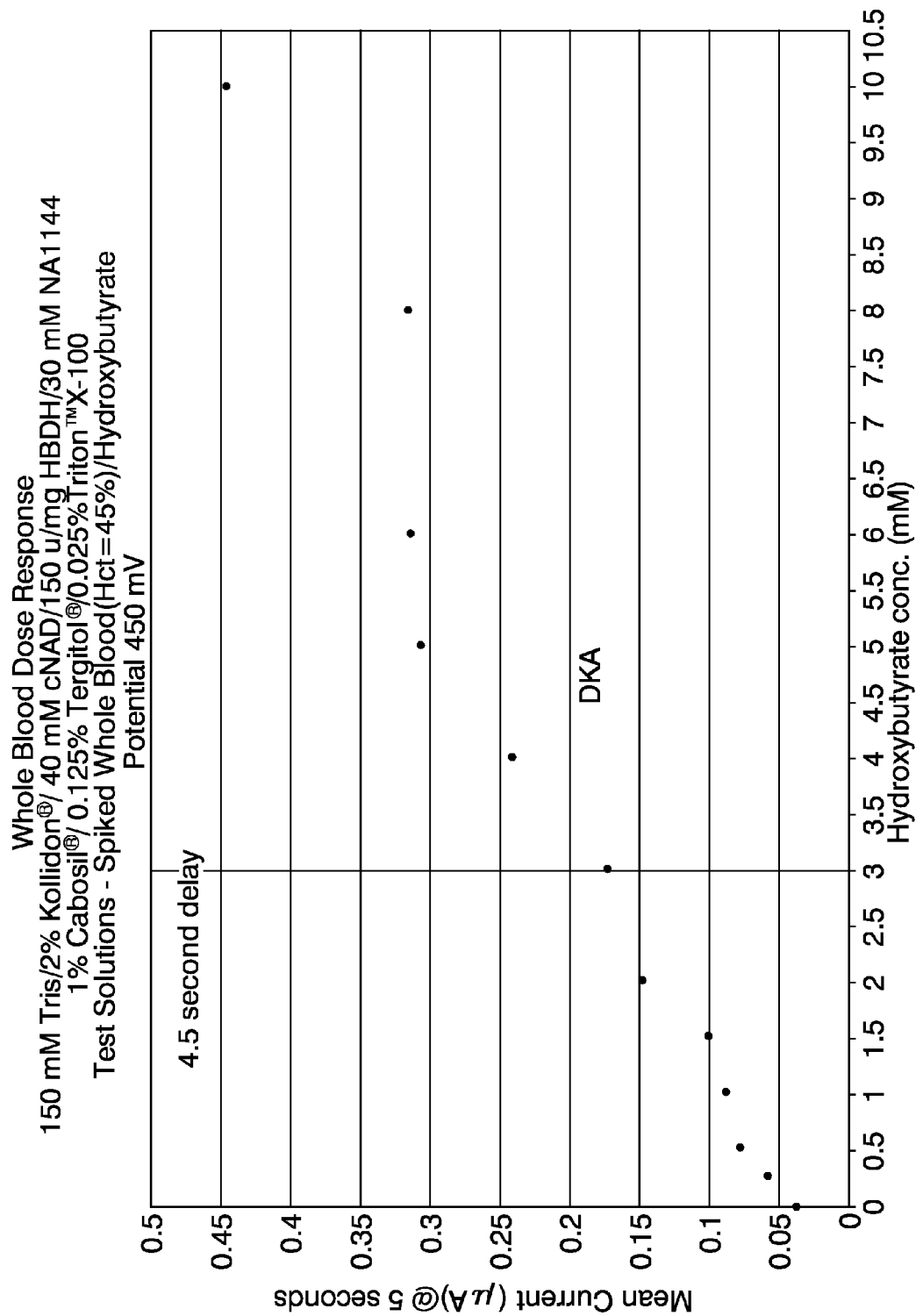

Reagent Material of FIG. 18

A nitrosoaniline/carba-NAD reagent material was prepared by adding the following ingredients to a 20 mL speed mixing cup containing 6.074 g of the Tris/Kollidon® buffer/polymer stock solution described above in connection with the reagent material of FIG. 10 in a serial fashion: a) 0.060 g of untreated fumed silica (Cabosil®, Cabot Corporation, Boston, Mass.) and b) 0.050 g of a substituted nitrosoaniline derivative (NA 1144 provided by Roche Diagnostics, Inc.) were added to the cup and the matrix was mixed for 1 minute at 24,000 rpm and the pH was adjusted to 7.8; c) 0.079 g of carba-NAD free acid was added to a 10 mL speed mixing cup containing 3 mL of the nitrosoaniline solution, and the matrix was mixed for 1 minute at 24,000 rpm and the pH was adjusted to 7.2; and d) 0.259 g of beta-hydroxybutyrate dehydrogenase from *alcaligenes faecalis* was added to the cup and speed mixed for 2 minutes at 24,000 rpm.

Preparation of Test Strips

Cards of ACCU-CHECK® Aviva brand electrodes with spacer and capillary designs were used to produce test strips. 1.5 µL of the reagent materials, described above, were dispensed into each electrode capillary channel using a PixSys™ SQ series dispensing system (Cartesian Technologies Irvine Calif.) and were dried for 1.5 minutes at 45° C. The dried cards were stored in a dry atmosphere overnight and strips of hydrophilic top foils were manually laminated onto the spacer layer over the capillary. The cards were then cut into individual sensors and stored in desiccated vials until use.

Preparation of Test Solutions

A stock phosphate saline buffer solution was prepared by adding 0.1829 g of potassium phosphate monobasic salt, 0.2007 g of potassium phosphate dibasic salt and 2.7956 g of potassium chloride to 200 mL of double distilled water and adjusting the solution's pH to 7.00. This solution was added to a 250 mL volumetric flask and diluted with double distilled water to make a 250 mL solution.

A 21 fold stock solution of hydroxybutyrate was prepared by adding 1.3372 g of hydroxybutyrate sodium salt to 40 mL of phosphate saline buffer solution. The solution was added to a 50 mL volumetric flask and diluted with phosphate saline buffer solution to 50 mL. The resulting stock solution was serially diluted with phosphate saline buffer to produce 11 hydroxybutyrate test stocks.

The final test solutions were prepared by spiking 1 mL of either phosphate saline or blood with 0.05 mL of the test stocks.

Kinetic Dose Responses

Whole blood or saline samples containing various levels of hydroxybutyrate (mM) were measured utilizing the test strips prepared above. The required potential (222 mV for Hexaammineruthenium strips and 450 mV for nitrosoaniline strips) was applied after contacting the sample on the strip. Total assay time was 6 seconds. The end point for the assay was taken 0.5 seconds (FIG. 7) and 5 seconds (FIGS. 9 and 10) after contacting the test strip with the sample.

End Point Dose Responses

Whole blood or saline samples containing various levels of hydroxybutyrate (0 to 10 mM) were measured using the test strips prepared above. The assay consisted of a 4.5 second delay after sample contact to the test strip followed by potential application, 450 mV for nitrosoaniline strips and 222 mV for the hexaammineruthenium strips for 6 seconds after the delay period. The end point for the assay was taken 5 seconds after contacting the test strip with the sample.

While not previously discussed, it should be appreciated that the relationship between hydroxybutyrate concentration and measured current facilitates utilization of the exemplary reagent materials to analyze hydroxybutyrate.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method of determining glucose and ketone values in a sample, the method comprising the steps of:
provproviding a test element configured for electrochemically determining glucose and ketone values in a sample;
contacting the test element with the sample, wherein the test element includes:
a first reagent material comprising a first coenzyme-dependent enzyme for determining the ketone value and at least one first reagent material coenzyme selected from the group consisting of thio-NAD, thio-NADP and a compound according to formula (I), wherein the first reagent material is associated with a first electrode system of the test element, and
a second reagent material comprising a second coenzyme-dependent enzyme for determining the glucose value and at least one second reagent material coenzyme selected from the group consisting of FAD, NAD, NADP, thio-NAD, thio-NADP and the compound according to formula (I), wherein the second reagent material is associated with a second electrode system of the test element,
wherein the compound according to formula (I) is as follows:

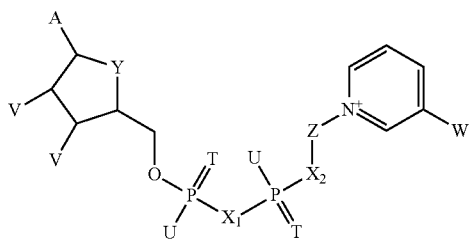

(I)

in which
A=adenine or an analog thereof,
T=in each case independently denotes O or S,
U=in each case independently denotes OH, SH, $BH_3^-$, or $BCNH_2^-$,
V=in each case independently denotes OH or a phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to $X_2$, and
where R4=in each case independently denotes H, F, Cl, or $CH_3$, provided that Z and the pyridine residue are not linked by a glycosidic bond,
or a salt or optionally a reduced form thereof;
applying a potential to the first and second electrode systems and measuring responses to the potential; and
determining from the measured responses the glucose and ketone values in the sample within 7.5 seconds or less after contacting the test element with the sample.

2. The method of claim 1, wherein the first coenzyme-dependent enzyme is a hydroxybutyrate dehydrogenase and the second coenzyme-dependent enzyme is a glucose dehydrogenase or a glucose oxidase.

3. The method of claim 1, wherein the step of determining glucose and ketone values in the sample is completed within 5 seconds after contacting the test element with the sample.

4. The method of claim 1, wherein the glucose and ketone values are determined within 2 seconds of one another during the determining step.

5. The method of claim 1, wherein the sample comprises blood.

6. The method of claim 2, wherein the hydroxybutyrate dehydrogenase is 3-hydroxybutyrate dehydrogenase.

7. The method of claim 1, wherein the at least one first reagent material coenzyme and the at least one second reagent material coenzyme is a compound according to formula (I):

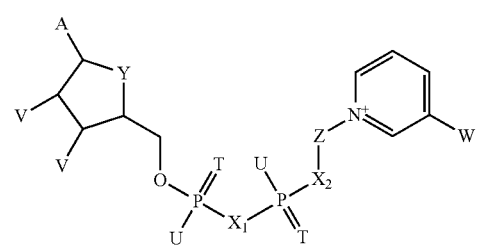

(I)

in which
A=adenine,
T=in each case denotes O,
U=in each case denotes OH,
V=in each case denotes OH,
W=$CON(R)_2$ in which R denotes H,
$X_1$=O,
$X_2$=O,
Y=O, and
Z=a carbocyclic 5-membered ring of the general formula (II)

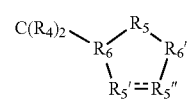

(II)

in which a single bond is present between R5' and R5", and in which
R4=H,
R5'=CHOH,
R5"=CHOH,
R5=$CR4_2$,
R6=CH, and
R6'=CH.

8. The method of claim 1, wherein the at least one first reagent material coenzyme and the at least one second reagent material coenzyme is a compound according to formula (I):

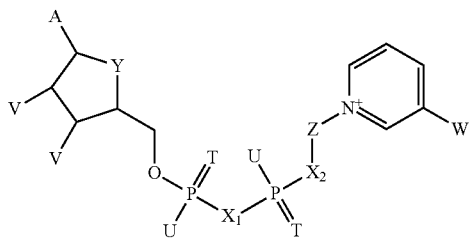

(I)

in which
A=adenine,
T=in each case denotes O,
U=in each case denotes OH,
V=in a first case denotes OH and in a second case denotes a phosphate group,
W=CON(R)$_2$ in which R denotes H,
X$_1$=O,
X$_2$=O,
Y=O, and
Z=a carbocyclic 5-membered ring of the general formula (II)

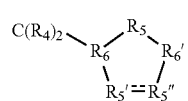

(II)

in which a single bond is present between R5' and R5", and in which
R4=H,
R5'=CHOH,
R5"=CHOH,
R5=CR4$_2$,
R6=CH, and
R6'=CH.

9. The method of claim 1, wherein the first reagent material further comprises a mediator selected from the group consisting of nitrosoaniline, potassium ferricyanide, and a combination of a phenazine compound and hexaammineruthenium chloride.

* * * * *